(12) United States Patent
Alcalde-Pais et al.

(10) Patent No.: US 8,217,041 B2
(45) Date of Patent: Jul. 10, 2012

(54) INDENE DERIVATIVES, THEIR PREPARATION AND USE AS MEDICAMENTS

(75) Inventors: Maria de las Ermitas Alcalde-Pais, Barcelona (ES); Jordi Frigola-Constansa, Barcelona (ES); Joerg Holenz, Barcelona (ES); Ramon Merce-Vidal, Barcelona (ES); Maria de les Neus Mesquida-Estevez, Barcelona (ES); Sara Lopez-Perez, Barcelona (ES)

(73) Assignee: Laboratories del Sr. Esteve, S.A. (ES)

( * ) Notice: Subject to any disclaimer, the term of this patent is extended or adjusted under 35 U.S.C. 154(b) by 930 days.

(21) Appl. No.: 12/093,100

(22) PCT Filed: Nov. 7, 2006

(86) PCT No.: PCT/EP2006/010627
§ 371 (c)(1),
(2), (4) Date: Aug. 7, 2008

(87) PCT Pub. No.: WO2007/054257
PCT Pub. Date: May 18, 2007

(65) Prior Publication Data
US 2009/0163547 A1   Jun. 25, 2009

Related U.S. Application Data

(60) Provisional application No. 60/735,042, filed on Nov. 8, 2005.

(30) Foreign Application Priority Data

Nov. 8, 2005 (ES) .................................. 200502720

(51) Int. Cl.
*A61K 31/50* (2006.01)
*A61K 31/435* (2006.01)
*C07D 221/18* (2006.01)
*C09B 5/00* (2006.01)

(52) U.S. Cl. .......... 514/247; 514/277; 514/416; 546/26; 548/416

(58) Field of Classification Search ............ 514/247, 514/277, 765; 546/26; 548/416
See application file for complete search history.

(56) References Cited

U.S. PATENT DOCUMENTS

| | | | |
|---|---|---|---|
| 3,692,325 A | 9/1972 | Gouirand | |
| 4,129,656 A | 12/1978 | Lang et al. | |
| 5,958,982 A | 9/1999 | Pamukcu et al. | |
| 5,965,619 A | 10/1999 | Pamukcu et al. | |
| 6,028,116 A | 2/2000 | Sperl et al. | |
| 6,159,996 A | 12/2000 | Jaehne et al. | |
| 6,177,471 B1 | 1/2001 | Menander et al. | |
| 2001/0006965 A1 | 7/2001 | Pamukcu et al. | |
| 2001/0020020 A1 | 9/2001 | Pamukcu et al. | |

FOREIGN PATENT DOCUMENTS

| | | |
|---|---|---|
| DE | 198 31 878 | 1/2000 |
| EP | 0 271 225 | 6/1988 |
| EP | 0 321 175 | 6/1989 |
| JP | 53 009752 | 1/1978 |
| JP | 61 060610 | 3/1986 |
| WO | WO 96/02537 | 2/1996 |
| WO | WO 96/03987 | 2/1996 |
| WO | WO 96/11929 | 4/1996 |
| WO | WO 96/23783 | 8/1996 |
| WO | WO 97/08167 | 3/1997 |
| WO | WO 02/41835 | 5/2002 |
| WO | WO 2004/048329 | 2/2004 |
| WO | WO 2005/040212 | 5/2005 |

OTHER PUBLICATIONS

Vippagunta et al. "Crystalline Solids" Advanced Drug Delivery Reviews 48 (2001) 3-26.*
International Search Report dated Aug. 8, 2007 relating to International Patent Application No. PCT/EP2006/010627.
Buckle et al., "Synthesis and smooth muscle relaxant activity of a new series of potassium channel activators: 3-amido-1, 1-dimethylindan-2-ols" Journal of Medicinal Chemistry, 34 (3), pp. 919-926; 1991, ISSN; 0022-2623.
Pullagurla et al., "Possible differences in modes of agonist and antagonist binding at human 5-HT6 receptors", BioOrganic and Medicinal Chemistry Letters, No. 14, 2004, pp. 4569-4573.
Kolanos et al., "Binding of isotryptamines and indenes at h5-HT6 serotinin receptors", BioOrganic and Medicinal Chemistry, vol. 15, Apr. 15, 2005, pp. 1987-1991.
Kwasi A. Ohemeng et al., "Receptor-based design of novel dihydrofolate reductase inhibitors: benzimidazole and indole derivaties", Journal of Medicinal Chemistry, 34 (4), pp. 1383-1394, 1991.

(Continued)

*Primary Examiner* — Renee Claytor
(74) *Attorney, Agent, or Firm* — Ostrolenk Faber LLP

(57) ABSTRACT

The present invention makes reference to new indene derivatives with general formula (I), as well as to their preparation procedures, their application as medicament and the pharmaceutical compositions containing them. The new compounds of formula (I) show affinity for $5\text{-HT}_6$ receptors and are, therefore, effective for treating diseases mediated by these receptors.

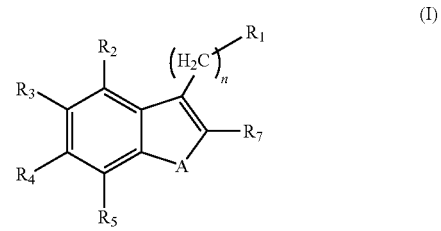

(I)

29 Claims, No Drawings

OTHER PUBLICATIONS

Olaf Kinzel et al., "A structure-guided approach to an Orthogonal Estrogen-Receptor-Based gene switch activated by ligands suitable for in vivo studies", Journal of Medicinal Chemistry, 49 (18), 5404-5407, 2006, ISSN: 0022-2623.

Dann L. Parker et al., "Triazolo-tetrahydrofluorenones as selective estrogen receptor beta agonists", BioOrganic and Medicinal Chemistry Letters, 16 (17), pp. 4652-4656, 2006.

Tasuo Oshiro et al., "Indanone oxime derivatives for the treatment of hypoxia", Chemical Abstracts Service, 1986.

Beilstein Institute for Organic Chemistry, XP002443333, Database Beilstein online.

Beilstein Institute for Organic Chemistry, XP002443336, Database Beilstein.

Beilstein Institute for Organic Chemistry, XP002443337, Database Beilstein.

Paul Gross et al., "Preparation of oxotetrahydrofuran lactone antitumor agents", Chemical Abstracts Service, 1996.

Kohji Fukatsu et al., "Synthesis of a Novel Series of Benzocycloalkene derivatives as melatonin receptor agonists", J. Med. Chem. 2002, 45, 4212-4221.

Roberto Perrone et al., "Mixed 5-$HT_{1A}$/D-2 activity of a new model of arylpiperazines: 1-aryl-4-[3-(1,2-dihydronaphthalen-4-yl)-n-propyl]piperazines. 1. Synthesis and structure-activity relationships", J. Med. Chem. 1994, 37, 99-104.

Michael R. Pranzatelli, M.D., "Serotonergic drugs and movement disorders in humans", Drugs of Today vol. 33, No. 6, 1997, pp. 379-392.

Ann Bourson et al., "Determination of the role of the 5-$HT_6$ receptor in the rat brain: A study using antisense oligonucleotides", Br. J. Pharmacol. Exp. Ther., 1995, 173-180.

Ruth Kohen et al., "Cloning, characterization, and chromosomal localization of a human 5-$HT_6$ serotonin receptor", Journal of Neurochemistry, 1996, 47-56.

Frederick J. Monsma, Jr. et al., "Cloning and expression of a novel serotonin receptor with high affinity for tricyclic psychotropic drugs", Mol. Pharmacol., 1993, 43, 320.

Martial Ruat et al., "A novel rat serotonin (5-$HT_6$) receptor: molecular cloning, localization and stimulation of $_c$amp accumulation", Biochem. Biophys. Res. Commun., 193(1), 1993, 268-276.

Takahiro Shinkai et al., "Association study of the 5-$HT_6$ receptor gene in schizophrenia", Am. J. Med. Gen. (Neuropsychiatric Genetics), 1999, 88:120-122.

A. J. Sleight et al., "Effects of altered 5-$HT_6$ expression in the rat: functional studies using antisense oligonucleotides", Behavioural Brain Research, 73, 1996, 245-248.

D.A. H. Taylor, "1, 2, 3, 4-tetrahydro-8-methylfluoren-1-one", J. Chem. Soc., Abstracts, 1960, 2805-2806.

M. L. Woolley et al., "A role for 5-$HT_6$ receptors in retention of spatial learning in the Morris water maze", Neuropharmacology 41, 2001, 210-219.

Caroline Gerard et al., "Immuno-localization of serotonin 5-$HT_6$ receptor-like material in the rat central nervous system", Brain Research 746, 1997, 207-219.

Charles E. Glatt et al., "Clozapine: selective labeling of sites resembling 5-$HT_6$ serotonin receptors may reflect psychoactive profile", Molecular Med., vol. 1, No. 4, May 1995, 398-406.

Warren D. Hirst et al., "Characterization of [$^{125}$I]-SB-258585 binding to human recombinant and native 5-$HT_6$ receptors in rat, pig and human brain tissue", British Journal of Pharmacology, 2000, 130, 1597-1605.

D. Hoyer et al., "5-HT receptor classification and nomenclature: towards a harmonization with the human genome", Neuropharmacology, 1997, vol. 36, No. 4/5, 419-128.

Bryan L. Roth et al., "Binding of typical and atypical antipsychotic agents to 5-hydroxytryptamine-6 and 5-hydroxytryptamine-7 receptors", J. Pharmacol. Exp. Ther., 1994, 268, 1403-1410.

Peter J. Munson et al., "LiGAND: A versatile computerized approach for characterization of Ligand-Binding systems", Analytical Biochemistry 1980, 107, 220-239.

Carol Routledge et al., "Characterization of SB-271046: A potent, selective and orally active 5-$HT_6$ receptor antagonist", British J. Pharmacol., 2000, 130, 1606-1612.

Anne Bourson et al., "Involvement of 5-$HT_6$ receptors in nigrostriatal function in rodents", British Journal of Pharmacology 1998, 125, 1562-1566.

Theresa A. Branchek et al., "5-$HT_6$ receptors as emerging targets for drug discovery", Annu. Rev. Pharmacol. Toxicol., 2000, 40, 319-334.

G.R. Clemo et al., "Indene Series: Part I. A synthesis of 1:2:3:8-tetrahydro-1-ketocyclopent[a]indene", J. Chem. Soc., Abstracts, 1951, 863-867.

D.C. Rogers et al., "Cognitive enhancement effects of the selective 5-$HT_6$ receptor antagonist SB-271046", Br. J. Pharmacol. Suppl., 1999, 127, 22P.

David L. Musso et al., "Indanylidenes. 1. Design and Synthesis of (E)-2-(4,6-Difluoro-1-indanylidene)acetamide, a potent, centrally acting muscle relaxant with antiinflammatory and analgesic activity", J. Med. Chem., 2003, 46, 399-408.

H. Ochiai, "Titanium (IV)-Mediated Aldol-Type condensation of zinc esters and zinc ketones with carbonyl electrophiles", J. Org. Chem., 1988, 53, 1343-1344.

Maik Finze et al., "Propylene polymerization with 1,2'-Bridged Bis(indenyl)zirconium dichlorides", macromolecules 2003, 36, 9325-9334.

M. Yoshioka et al., "Central distribution and function of 5-$HT_6$ receptor subtype in the rat brain", Ann., NY Acad. Sci., 1998, 861, 244.

* cited by examiner

INDENE DERIVATIVES, THEIR PREPARATION AND USE AS MEDICAMENTS

CROSS REFERENCE TO RELATED APPLICATIONS

The present application is a 35 U.S.C. §§371 national phase conversion of PCT/EP2006/010627, filed Nov. 7, 2006, which claims priority of U.S. Provisional Patent Application No. 60/735,042, filed Nov. 8, 2005, and Spanish Patent Application No. P200502720, filed Nov. 8, 2005, the disclosures of which have been incorporated herein by reference. The PCT International Application was published in the English language.

FIELD OF THE INVENTION

The present invention relates to new indene derivatives with a general formula (I), as well as to their preparation procedure, their application as medicaments and to the pharmaceutical compositions comprising them.

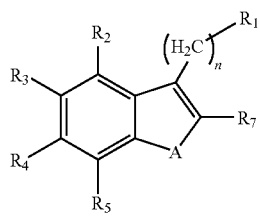

The new compounds of formula I show affinity for $5\text{-}HT_6$ receptors and are, therefore, effective for treating diseases mediated by these receptors.

BACKGROUND OF THE INVENTION

The superfamily of 5-HT serotonin receptors includes 7 classes ($5\text{-}HT_1\text{-}5\text{-}HT_7$) which encompass 14 subclasses [D. Hoyer, et al., *Neuropharmacology*, 1997, 36, 419]. The $5\text{-}HT_6$ receptor is the latest serotonin receptor identified by molecular cloning both in rats [F. J. Monsma, et al., *Mol. Pharmacol.*, 1993, 43, 320; M. Ruat, et al., *Biochem. Biophys. Res. Commun.*, 1993, 193, 268] and humans [R. Kohen, et al., *J. Neurochem.*, 1996, 66, 47]. Compounds that show affinity for $5\text{-}HT_6$ receptors are suitable for the treatment of several disorders of the central nervous system and the gastrointestinal tract, such as irritable bowel syndrome. Compounds with affinity for $5\text{-}HT_6$ receptors are also suitable for treating anxiety, depression and cognitive memory disorders [M. Yoshioka, et al., *Ann. NY Acad. Sci.*, 1998, 861, 244; A. Bourson, et al., *Br. J. Pharmacol.*, 1998, 125, 1562; D. C. Rogers, et al., *Br. J. Pharmacol. Suppl.*, 1999, 127, 22P; A. Bourson, et al., *J. Pharmacol. Exp. Ther.*, 1995, 274, 173; A. J. Sleight, et al., *Behav. Brain Res.*, 1996, 73, 245; T. A. Branchek, et al., *Annu. Rev. Pharmacol. Toxicol.*, 2000, 40, 319; C. Routledge, et al., *Br. J. Pharmacol.*, 2000, 130, 1606]. It has been shown that typical and atypical antipsychotic drugs used to treat schizophrenia have a high affinity for 5-HT6 receptors [B. L. Roth, et al., *J. Pharmacol. Exp. Ther.*, 1994, 268, 1403; C. E. Glatt, et al., *Mol. Med.*, 1995, 1, 398; F. J. Mosma, et al., *Mol. Pharmacol.*, 1993, 43, 320; T. Shinkai, et al., *Am. J. Med. Genet.*, 1999, 88, 120]. Compounds with affinity for $5\text{-}HT_6$ receptors are also suitable for treating infantile hyperkinesia (ADHD; Attention Deficit/Hyperactivity Disorder) [W. D. Hirst, et al., *Br. J. Pharmacol.*, 2000, 130, 1597; C. Gérard, et al., *Brain Research*, 1997, 746, 207; M. R. Pranzatelli, *Drugs of Today*, 1997, 33, 379]. It has also been shown that $5\text{-}HT_6$ receptors also play a role in the intake of nutrients [*Neuropharmacology*, 2001, 41, 210-219]. Eating disorders, particularly obesity, are a serious and growing threat to public health in all age groups, as they increase the risk of developing other more serious diseases that endanger the life of patients, such as diabetes or coronary diseases.

Several patent documents refer to compounds with affinity for receptors of the 5-HT superfamily. Documents WO 96/23783, WO 96/02537, WO 96/11929 and WO 97/08167 describe heterocyclic compounds antagonists of 5-HT2b/2c receptors.

On another hand, there are other patent documents that have described indene derivatives with therapeutic activity. U.S. Pat. No. 5,092,827, U.S. Pat. No. 6,025,394, U.S. Pat. No. 5,958,982, U.S. Pat. No. 5,965,619, U.S. Pat. No. 6,028,116, US 2001/0006965 and US 2001/0020020 describe indene derivatives as being suitable for treating psoriasis, acne, sarcoidosis, pre-cancerous lesions and neoplasias, as well as diabetic retinopathy and macular degeneration. The therapeutic effect of these compounds seems to originate in their inhibitive action on a specific phosphodiesterase of cGMP (cGMP PDE), as described in the U.S. Pat. No. 6,177,471.

Surprisingly, the authors of the present invention have observed that indene derivative compounds with general formula (I) show an affinity for $5\text{-}HT_6$ receptors ranging from good to excellent. These compounds are therefore particularly suitable as pharmacologically active agents in medicaments for the prophylaxis and/or treatment of disorders or diseases related to $5\text{-}HT_6$ receptors.

OBJECT OF THE INVENTION

First of all, an object of the present invention is an indene derivative of general formula I:

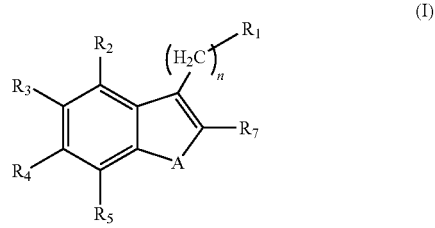

Compounds with general formula I have shown a high affinity for $5HT_6$ receptors and thus provide a good therapeutic alternative for treating disorders mediated by said receptors.

Another object of the present invention is the procedures for preparing the indene derivatives of general formula I. As will be seen further below, the present application describes the procedures for obtaining the compounds (Ia), (Ib), (Ic), (Id), (Ie), (If), (Ig), (Ih), (Ik) and (In), specific embodiments of the compounds of general formula I. Specifically, to obtain the compounds (Ia) and (Ib) more than one possible procedure is described.

An additional object of the present invention is the intermediates of general formula (II):

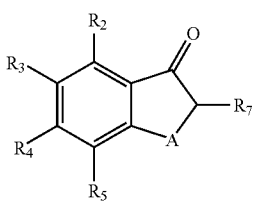

for obtaining the compounds of formula (I)

Likewise, the use of indene derivatives of general formula (I) in the manufacture of a medicament for treating disorders or diseases mediated by $5HT_6$ receptors is an object of the present invention. Among the diseases or disorders mediated by $5HT_6$ receptors for which indene derivatives of general formula I are useful are disorders or diseases related to food intake, preferably those related to appetite regulation, maintaining, increasing or reducing body weight, obesity, bulimia, anorexia, cachexia or diabetes type II, or irritable bowel syndrome; disorders of the central nervous system; anxiety; panic attacks; depression; bipolar disorders; cognitive disorders; memory disorders; senile dementia; psychosis; schizophrenia; neurodegenerative disorders, preferably selected among Alzheimer's disease, Parkinson's disease, Huntington's disease and multiple sclerosis; or hyperactivity disorders, preferably attention deficit/hyperactivity disorder or for improving cognitive capacity.

A final object of the present invention is a pharmaceutical composition comprising an indene derivative of general formula I and at least one pharmaceutically acceptable additive. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

A first aspect makes reference to an indene derivative of general formula I:

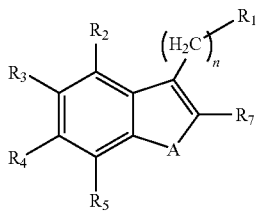

where
n is 0, 1, 2, 3 or 4
$R^1$ represents a saturated or unsaturated cycloaliphatic radical, optionally at least monosubstituted, optionally at least with one heteroatom selected among N, O and S as a member of the ring that may be condensed with a mono or polycyclic annular system optionally at least monosubstituted; a —$NR^8R^9$ radical; a —$CONR^8R^9$ radical; —COOH; or —OH where $R^8$ and $R^9$ represent, independently of each other, a hydrogen atom; or a linear or branched, saturated or unsaturated $C_{1-5}$ aliphatic radical that may be substituted with 1, 2, 3 substituents selected independently among F, Cl, Br, —OH, —$NH_2$, —SH, —O—$CH_3$, —O—$C_2H_5$, —$NO_2$, —CN, —NH—$CH_3$ and —S—$CH_3$;

or $R^8$ and $R^9$ together with nitrogen atom form a saturated, unsaturated or aromatic heterocyclic ring with 3 to 9 members, which may be substituted with 1, 2 or 3 substituents selected independently from $C_{1-5}$-alkyl, —O—$C_{1-5}$-alkyl, —S—$C_{1-5}$-alkyl, oxo (=O), thioxo (=S), —C(=O)—OH, —C(=O)—O—$C_{1-5}$-alkyl, —O—C(=O)—$C_{1-5}$-alkyl, F, Cl, Br, I, —CN, —$CF_3$, —$OCF_3$, —$SCF_3$, —OH, —SH, —$NH_2$, —NH($C_{1-5}$-alkyl), —N($C_{1-5}$-alkyl)$_2$, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl and which may contain 1, 2 or 3 additional heteroatoms independently selected among N, O and S as members of the ring $R^2$, $R^3$, $R^4$ and $R^5$ represent, independently of one another, a hydrogen atom; —$NO_2$; —$NH_2$; —SH; —OH; —CN; —C(=O)—H; —C(=O)—$R^{10}$; —$OR^{11}$; —$SR_{12}$; —$SOR^{13}$, —S(=O)$_2$—$R^{13}$, —S(=O)$_2$—N($R^{14}$)$R^{15}$, —N($R^{16}$)—S(=O)$_2$—$R^{17}$; —NH—$R^{18}$; —$NR^{19}R^{20}$; —N($R^{21}$)—CO—$R^{22}$; F; Cl, Br; I; a $C_1$-$C_6$ aliphatic radical, linear or branched, saturated or unsaturated, which may be substituted by 1, 2 or 3 substituents independently selected among F, Cl, Br, —OH, —$NH_2$, —SH, —O—$CH_3$, —O—$C_2H_5$, —$NO_2$, —CN, —NH—$CH_3$ and —S—$CH_3$; or an aryl or heteroaryl radical of 5 to 14 members, which may be substituted with 1, 2 or 3 substituents independently selected among —$CF_3$, $C_{1-5}$-alkyl, —O—$C_{1-5}$-alkyl, —S—$C_{1-5}$-alkyl, —C(=O)—OH, —C(=O)—O—$C_{1-5}$-alkyl, —O—C(=O)—$C_{1-5}$-alkyl, F, Cl, Br, I, —CN, —$OCF_3$, —$SCF_3$, —OH, —SH, —$NH_2$, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy, benzyloxy and benzyl and which may be bonded by a linear or branched $C_1$-$C_6$ alkylene group, and where the heteroaryl radical contains 1, 2 or 3 heteroatoms independently selected among N, O and S as members of the ring;

with the condition that at least one of the substituents $R^2$, $R^3$, $R^4$ and $R^5$ represents a —$NO_2$, —$SOR^{13}$, —S(=O)$_2$—$R^{13}$, —S(=O)$_2$—N($R^{14}$)$R^{15}$, —N($R^{16}$)—S(=O)$_2$—$R^{17}$, —N($R^{21}$)—CO—$R^{22}$ radical;

A represents:

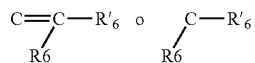

which respectively means (Ix) and (Iy) type compounds:

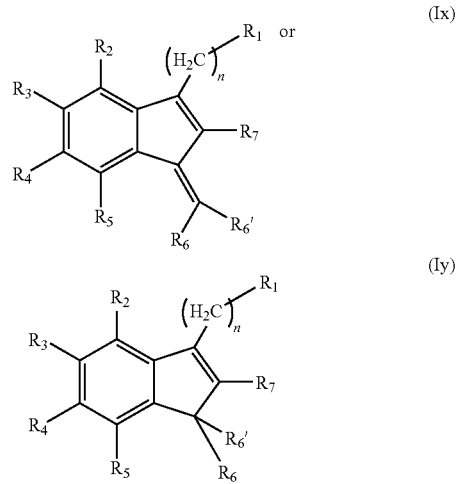

$R^6$ and $R'_6$, identical or different, represent a hydrogen atom; $NO_2$; $—NH_2$; $—SH$; $—OH$; $—CN$; $—C(=O)—R^{10}$; $—OR^{11}$; $—SR^{12}$; F; Cl, Br; I; a linear or branched, saturated or unsaturated $C_1$-$C_{10}$ aliphatic radical, which may be substituted with 1, 2 or 3 substituents independently selected among F, Cl, Br, —OH, —SH, —O—$CH_3$, —O—$C_2H_5$, —$NO_2$, —CN and —S—$CH_3$; or an aryl or heteroaryl radical with 5 to 14 members that may be substituted with 1, 2 or 3 substituents independently selected among —$CF_3$, $C_{1-5}$-alkyl, —O—$C_{1-5}$-alkyl, —S—$C_{1-5}$-alkyl, —C(=O)—OH, —C(=O)—O—$C_{1-5}$-alkyl, —O—C(=O)—$C_{1-5}$-alkyl, F, Cl, Br, I, —CN, —$OCF_3$, —$SCF_3$, —OH, —SH, —$NH_2$, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy, benzyloxy and benzyl and which may be bonded through a $C_1$-$C_6$ alkylene, $C_2$-$C_6$ alkenylene or $C_1$-$C_6$ ilidene linear or branched groups and where the heteroaryl radical contains 1, 2 or 3 heteroatoms independently selected from among N, O and S as members of the ring;

$R^7$ represents a hydrogen atom, a $C_1$-$C_6$ linear or branched aliphatic radical which may be substituted with 1, 2 or 3 substituents independently selected among F, Cl, Br, —OH, —SH, —O—$CH_3$, —O—$C_2H_5$, —$NO_2$, —CN and —S—$CH_3$;

$R^{10}$ to $R^{22}$ represent, independently of each other, a hydrogen atom; a linear or branched, saturated or unsaturated $C_1$-$C_5$ aliphatic radical, which may be substituted with 1, 2 or 3 substituents independently selected from F, Cl, Br, —OH, —$NH_2$, —SH, —O—$CH_3$, —O—$C_2H_5$, —$NO_2$, —CN, —NH—$CH_3$ and —S—$CH_3$; a saturated or unsaturated cycloaliphatic radical with 3 to 8 members, which may be substituted with 1, 2 or 3 substituents independently selected from $C_{1-5}$-alkyl, —O—$C_{1-5}$-alkyl, —S—$C_{1-5}$-alkyl, oxo (=O), thioxo (=S), —C(=O)—OH, —C(=O)—O—$C_{1-5}$-alkyl, —O—C(=O)—$C_{1-5}$-alkyl, F, Cl, Br, I, —CN, —$CF_3$, —$OCF_3$, —$SCF_3$, —OH, —SH, —$NH_2$, —NH($C_{1-5}$-alkyl), —N($C_{1-5}$-alkyl)$_2$, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy benzyloxy and benzyl and which optionally may include 1, 2 or 3 heteroatoms independently selected among N, O and S as members of the ring and which may be bonded through a linear or branched $C_1$-$C_6$ alkylene group; or an aryl or heteroaryl radical with 5 to 14 members that may be substituted with 1, 2 or 3 substituents independently selected from —$CF_3$, $C_{1-5}$-alkyl, —O—$C_{1-5}$-alkyl, —S—$C_{1-5}$-alkyl, —C(=O)—OH, —C(=O)—O—$C_{1-5}$-alkyl, —O—C(=O)—$C_{1-5}$-alkyl, F, Cl, Br, I, —CN, —$OCF_3$, —$SCF_3$, —OH, —SH, —$NH_2$, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy, benzyloxy and benzyl and which may be bonded through a linear or branched $C_1$-$C_6$ alkylene, $C_2$-$C_6$ alkenylene or $C_2$-$C_6$ alkynylene group and where the heteroaryl radical contains 1, 2 or 3 heteroatoms independently selected from N, O and S as members of the ring;

preferably with the condition that when $R^1$ is —COOH; $R^2$, $R^3$, $R^4$ or $R^5$ are not —$SOR^{13}$, —S(=O)$_2$—$R^{13}$ or —S(=O)$_2$—N($R^{14}$)$R^{15}$ and that A does not represent C=C (R6) $R_6'$ resulting in the simultaneous situation in which R6 or $R_6'$ are one H and the other a phenyl substituted with —S(=O)$_2$—$C_{1-5}$-alkyl, —$NH_2$, —O—$C_{1-5}$-alkyl, F, Cl, Br, CN, —C(=O)—OH or —C(=O)—O—$C_{1-5}$-alkyl, or the situation in which both $R_6$ and $R_6'$ represent —$OR^{11}$, and/or preferably with the condition that when $R^1$ is —OH; $R^2$, $R^3$, $R^4$ or $R^5$ are not —S(=O)$_2$—$R^{13}$ or —S(=O)$_2$—N($R^{14}$)$R^{15}$, and/or preferably with the condition that when $R^1$ is —$CONR^8R^9$; $R^2$, $R^3$, $R^4$ or $R^5$ are not —$SOR^{13}$, —S(=O)$_2$—$R^{13}$ or —S(=O)$_2$—N($R^{14}$)$R^{15}$ and that A does not represent C=C (R6) $R_6'$ resulting in the simultaneous situation in which R6 or $R^{6'}$ are one H and the other a phenyl substituted with —S(=O)$_2$—$C_{1-5}$-alkyl, —$NH_2$, —O—$C_{1-5}$-alkyl, F, Cl, Br, I, CN, —C(=O)—OH or —C(=O)—O—$C_{1-5}$-alkyl, an aryl or a heteroaryl, and/or preferably with the condition that when $R^1$ is —$NR^8R^9$; $R^2$, $R^3$, $R^4$ or $R^5$ are not —$SOR^{13}$ or —S(=O)$_2$—$R^{13}$ and that A does not represent C=C(R6) $R_6'$ resulting in the simultaneous situation in which R6 or $R_6'$ are one H and the other a phenyl substituted with —S(=O)$_2$—$C_{1-5}$-alkyl, —$NH_2$, —O—$C_{1-5}$-alkyl, F, Cl, Br, CN, —C(=O)—OH or —C(=O)—O—$C_{1-5}$-alkyl or a pharmaceutically acceptable salt, isomer, prodrug or solvate thereof, optionally in the form of one of their stereoisomers, preferably enantiomers or diastereomers, a racemate or in the form of a mixture of at least two stereoisomers, preferably enantiomers and/or diastereomers, in any mixing ratio or a physiologically acceptable salt thereof or the corresponding solvate thereof.

The term "salt" must be understood as any form of an active compound used in accordance with this invention in which the said compound is in ionic form or is charged and coupled to a counter-ion (a cation or anion) or is in solution. This definition also includes quaternary ammonium salts and complexes of the active molecule with other molecules and ions, particularly complexes formed via ionic interactions. The definition particularly includes physiologically acceptable salts; this term must be understood as equivalent to "pharmacologically acceptable salts".

The term "physiologically acceptable salts" in the context of this invention means any salt that is tolerated physiologically (normally meaning that it is not toxic, particularly as a result of the counter-ion) when used in an appropriate manner for a treatment, particularly applied or used in humans and/or mammals.

These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are particularly preferred, as well as those formed with ammonium cations ($NH_4^+$). Preferred salts are those formed with (mono) or (di)sodium, (mono) or (di)potassium, magnesium or calcium.

These physiologically acceptable salts may be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), especially including hydrates and alcoholates, for example methanolate.

In a specific and preferred embodiment of the invention $R^1$ represents:

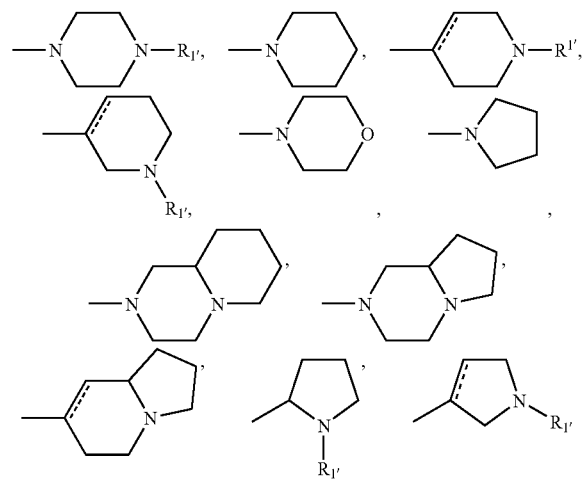

where the dotted line represents an optional chemical bond and $R'_1$, represents a hydrogen atom, a $C_{1-5}$ aliphatic radical or a protective group such as benzyl.

In another preferred embodiment of the invention $R^1$ represents a —$NR^8R^9$ radical and $R^8$ and $R^9$ represent independently or together a hydrogen atom or a $C_{1-5}$ aliphatic radical.

In another preferred embodiment of the invention $R^1$ represents a —$NR^8R^9$ radical; and $R^8$ and $R^9$ together with nitrogen form a saturated, unsaturated or aromatic heterocyclic ring with 3 to 9 members that optionally contains 1, 2 or 3 additional heteroatoms independently selected from N, O and S.

Another preferred embodiment of the invention defines those compounds of formula I in which $R^1$ represents a —$CONR^8R^9$ radical; and $R^8$ and $R^9$ represent independently or together a hydrogen atom or a $C_{1-5}$ aliphatic radical.

Another preferred embodiment are compounds of formula I in which $R^1$ represents a —$CONR^8R^9$ radical; and $R^8$ and $R^9$ together with nitrogen form a saturated, unsaturated or aromatic heterocyclic ring with 3 to 9 members that optionally contains 1, 2 or 3 additional heteroatoms independently selected from N, O and S.

In addition, indene derivatives of general formula I in which at least one of among $R^2$, $R^3$, $R^4$ or $R^5$ represents a —$SOR^{13}$ radical are also preferred.

Another preferred embodiment is that in which at least one of $R^2$, $R^3$, $R^4$ or $R^5$ represents a —$S(=O)_2$—$R^{13}$ radical.

Another preferred embodiment is that in which at least one of $R^2$, $R^3$, $R^4$ or $R^5$ represents a —$S(=O)_2$—$N(R^{14})R^{15}$ radical.

Also considered a preferred embodiment is that in which at least one of $R^2$, $R^3$, $R^4$ or $R^5$ represents a —$N(R^{16})$—$S(=O)_2$—$R^{17}$ radical.

Another preferred embodiment is that in which at least one of $R^2$, $R^3$, $R^4$ or $R^5$ represents a —$N(R^{21})$—CO—$R^{22}$ radical.

With regards to other substituents such as $R^6$ and $R'_6$, an indene derivative of general formula I is preferred wherein $R^5$ and $R'_6$, identical or different, represent a hydrogen atom, a $C_{1-5}$ aliphatic radical or an aryl or heteroaryl radical with 5 to 14 members optionally substituted with a phenyl that may be bonded by a $C_1$-$C_6$ alkylene or a $C_1$-$C_6$ ylidene.

Lastly, compounds with general formula I are preferred in which $R^{10}$ to $R^{22}$ represent an aryl or heteroaryl radical with 1, 2 or 3 heteroatoms independently selected among N, O and S and which may be substituted by a Cl.

Among all the compounds described in the general formula I, particularly preferred are any of those selected from:

[1] (2-methyl-6-nitro-3H-inden-1-yl)acetic acid
[2] [2-methyl-6-(naphthalene-2-sulphonylamino)-3H-inden-1-yl]acetic acid
[3] [3(Z)-benzylidene-2-methyl-6-(naphthalene-2-sulphonylamino)-3H-inden-1-yl]acetic acid
[4] [2-methyl-4-(naphthalene-2-sulphonylamino)-3H-inden-1-yl]acetic acid
[5] [6-(naphthalene-2-sulphonylamino)-3H-inden-1-yl]acetic acid
[6] [6-(5-chloro-3-methylbenzo[b]thiophene-2-sulphonylamino)-2-methyl-3H-inden-1-yl]acetic acid
[7] [2-methyl-6-(naphthalene-1-ylsulfamoyl)-3H-inden-1-yl]acetic acid
[8] N,N-Dimethyl-2-(2-methyl-6-nitro-3H-inden-1-yl)acetamide
[9] 2-(2-Methyl-6-nitro-3H-inden-1-yl)-1-pyrrolidin-1-ylethanone
[10] 2-[3(Z)-Benzylidene-2-methyl-6-(naphthalene-2-sulphonylamino)-3H-inden-1-yl]-N,N-dimethyl acetamide
[11] N,N-Dimethyl-2-[2-methyl-6-(naphthalene-2-sulphonylamino)-3H-inden-1-yl]acetamide
[12] N-[2-Methyl-3-(2-oxo-2-pyrrolidin-1-ylethyl)-1H-inden-5-yl]naphthalene-2-sulfonamide
[13] N-[2-Methyl-1-(2-oxo-2-pyrrolidin-1-ylethyl)-3H-inden-4-yl]naphthalene-2-sulfonamide

[14] N-[3-(2-Oxo-2-pyrrolidin-1-ylethyl)-1H-inden-5-yl]naphthalene-2-sulfonamide
[15] N-[2-Methyl-3-(2-oxo-2-pyrrolidin-1-ylethyl)-1H-inden-5-yl]-5-chloro-3-methylbenzo[b]thiophene-2-sulfonamide
[16] N,N-Dimethyl-2-[2-methyl-6-(naphthalene-1-ylsulfamoyl)-3H-inden-1-yl]acetamide
[17] Dimethyl-[2-(2-methyl-6-nitro-3H-inden-1-yl)ethyl]amine
[18] 3-(2-Dimethylaminoethyl)-2-methyl-1H-inden-5-ylamine
[19] N-[3-(2-Dimethylaminoethyl)-2-methyl-1H-inden-5-yl]-6-chloroimidazo[2,1-b]thiazole-5-sulfonamide
[20] N-[3-(2-Dimethylaminoethyl)-2-methyl-1H-inden-5-yl]-5-chloro-3-methylbenzo[b]thiophene-2-sulfonamide
[21] N-{4-[3-(2-Dimethylaminoethyl)-2-methyl-1H-inden-5-ylsulfamoyl]phenyl}acetamide
[22] N-[3-(2-Dimethylaminoethyl)-2-methyl-1H-inden-5-yl]benzo[1,2,5]thiadiazole-4-sulfonamide
[23] N-Ethyl-N-[3-(2-dimethylaminoethyl)-2-methyl-1H-inden-5-yl]-5-chloro-3-methylbenzo[b]thiophene-2-sulfonamide
[24] 4-Amino-N-[3-(2-dimethylaminoethyl)-2-methyl-1H-inden-5-yl]benzene sulfonamide
[25] N-[3-(2-Pyrrolidin-1-ylethyl)-2-methyl-1H-inden-5-yl]-2-(4-benzyloxyphenyl)acetamide
[26] 2-Methyl-3-(2-pyrrolidin-1-ylethyl)-1H-inden-5-ylamine
[27] (2-{6-[(5-chloro-3-methylbenzo[b]thiophene-2-sulfonyl)ethylamino]-2-methyl-3H-inden-1-yl}ethyl)ethyldimethylammonium iodide
[28] 1-[2-(2-Methyl-6-nitro-3H-inden-1-yl)ethyl]pyrrolidine
[29] N-[3-(2-Pyrrolidin-1-ylethyl)-2-methyl-1H-inden-5-yl]-6-chloroimidazo[2,1-b]thiazole-5-sulfonamide
[30] N-{4-[3-(2-Pyrrolidin-1-ylethyl)-2-methyl-1H-inden-5-ylsulfamoyl]phenyl}acetamide
[31] N-[3-(2-Pyrrolidin-1-ylethyl)-2-methyl-1H-inden-5-yl]-benzo[1,2,5]thiadiazole-4-sulfonamide
[32] 4-Amino-N-[3-(2-pyrrolidin-1-ylethyl)-2-methyl-1H-inden-5-yl]benzene sulfonamide
[33] N-[1(Z)-Benzylidene-3-(2-dimethylaminoethyl)-2-methyl-1H-inden-5-yl]naphthalene-2-sulfonamide
[34] N-[3-(2-Dimethylaminoethyl)-2-methyl-1H-inden-5-yl]naphthalene-2-sulfonamide
[35] N-[2-Methyl-3-(2-pyrrolidin-1-ylethyl)-1H-inden-5-yl]naphthalene-2-sulfonamide
[36] N-[2-Methyl-1-(2-pyrrolidin-1-ylethyl)-3H-inden-4-yl]naphthalene-2-sulfonamide
[37] N-[3-(2-Pyrrolidin-1-ylethyl)-1H-inden-5-yl]naphthalene-2-sulfonamide
[38] N-[2-Methyl-3-(2-pyrrolidin-1-ylethyl)-1H-inden-5-yl]-5-chloro-3-methylbenzo[b]thiophene-2-sulfonamide
[39] N-(Naphthalene-1-yl)-3-(2-dimethylaminoethyl)-2-methyl-1H-indene-5-sulfonamide
[40] N-[3-(2-Hydroxyethyl)-2-methyl-1H-inden-5-yl]naphthalene-2-sulfonamide
[41] 6-Chloro-N-{3-[2-(dimethylamino)ethyl]-1,1-dimethyl-1H-inden-5-yl}imidazo[2,1-b] [1,3]thiazole-5-sulfonamide
[42] 5-Chloro-N-{3-[2-(dimethylamino)ethyl]-1,1-dimethyl-1H-inden-5-yl}-3-methylbenzo[b]thiophene-2-sulfonamide
[43] N-{3-[2-(Dimethylamino)ethyl]-2-methyl-1H-inden-5-yl}naphthalene-1-sulfonamide
[44] N-{3-[2-(Dimethylamino)ethyl]-2-methyl-1H-inden-5-yl}-1-benzothiophene-3-sulfonamide
[45] 6-Chloro-N-[2-methyl-3-(1-methylpyrrolidin-3-yl)-1H-inden-5-yl]imidazo[2,1-b] [1,3]thiazole-5-sulfonamide
[46] 6-Chloro-N-[2-methyl-3-(1-methylpiperidin-3-yl)-1H-inden-5-yl]imidazo[2,1-b] [1,3]thiazole-5-sulfonamide
[47] 2-(5-Chloro-2-methyl-1H-inden-3-yl)-N,N-dimethylethanamine
[48] 6-Chloro-N-{3-[2-(dimethylamino)ethyl]-1H-inden-5-yl}imidazo[2,1-b] [1,3]thiazole-5-sulfonamide
[49] 6-Chloro-N-[3-(2-piperidin-1-ylethyl)-1H-inden-5-yl]imidazo[2,1-b] [1,3]thiazole-5-sulfonamide
[50] 6-Chloro-N-[3-(1-methylpyrrolidin-3-yl)-1H-inden-5-yl]imidazo[2,1-b] [1,3]thiazole-5-sulfonamide A specific embodiment of the invention is that in which the indene derivatives of the invention represent a compound with the general formula (Ia):

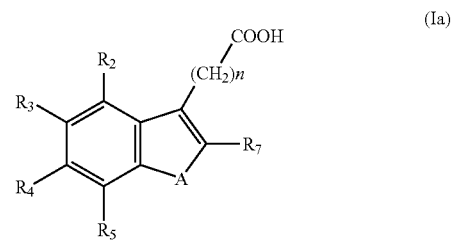

where $R^2$, $R^3$, $R^4$, $R^5$, $R^7$, A, and n have the previously described meanings.

Also a specific embodiment is one in which the indene derivatives of the invention are represented by the general formula (Ib):

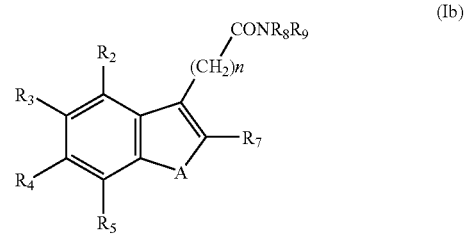

where $R^2$, $R^3$, $R^4$, $R^5$, $R^7$, $R^8$, $R^9$, A, and n have the previously described meanings.

In addition, another specific embodiment is provided by the indene derivatives of general formula (Ic):

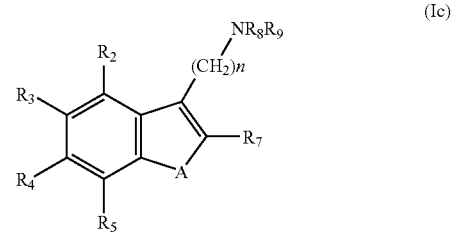

where $R^2$, $R^3$, $R^4$, $R^5$, $R^7$, $R^8$, $R^9$, A, and n have the previously mentioned meanings.

Another specific embodiment of the invention are the compounds with the general formula (Id):

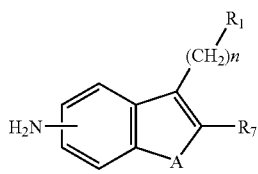

(Id)

where the amine group can be at any position in the benzene ring and the other positions which can be substituted as described above for formula I, preferably hydrogen, $-OR_{11}$, $-SR_{11}$, F, Cl, Br, I or a $C_{1-4}$ alkyl radical, and where $R_1$, $R_7$, $R_{11}$, A and n have the previously mentioned meanings.

Another specific embodiment is that in which the compounds of the invention have the general formula (Ie):

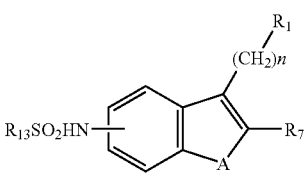

(Ie)

where $-NHSO_2R_{13}$ can be at any position in the benzene ring and the other positions can be substituted as described above for formula I, preferably hydrogen, $-OR_{11}$, $-SR_{11}$, F, Cl, Br, I or a $C_{1-4}$ alkyl radical, and where $R_1$, $R_7$, $R_{11}$, $R_{13}$, A and n have the previously mentioned meanings.

Another specific embodiment of the invention are the indene derivatives with the general formula (If):

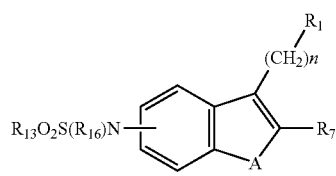

(If)

where $-N(R_{16})SO_2R_{13}$ can be at any position in the benzene ring and the other positions can be substituted as described above for formula I, preferably hydrogen, $-OR_{11}$, $-SR_{11}$, F, Cl, Br, I or a $C_{1-4}$ alkyl radical, and where $R_1$, $R_7$, $R_{11}$, $R_{13}$, $R_{16}$, A and n have the previously mentioned meanings.

Another specific embodiment are indene derivatives with the general formula (Ig):

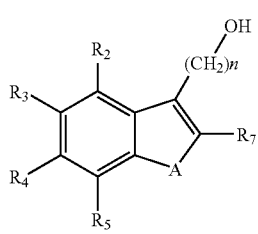

(Ig)

where $R_2$, $R_3$, $R_4$, $R_5$, $R_7$, A have the previously mentioned meanings and n=1, 2, 3, 4

Another specific embodiment of the invention are the compounds with the general formula (Ih):

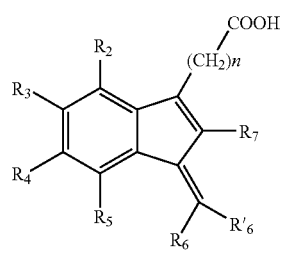

(Ih)

where $R_2$, $R_3$, $R_4$, $R_5$, $R_6$, $R_{6'}$, $R_7$ and n have the previously mentioned meanings.

Another specific embodiment of the invention are the compounds with the general formula (In):

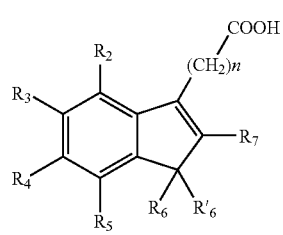

(In)

where $R_2$, $R_3$, $R_4$, $R_5$, $R_6$, $R_{6'}$, $R_7$ and n have the previously mentioned meanings.

Finally, another specific execution of the invention are the compounds with the general formula (Ik):

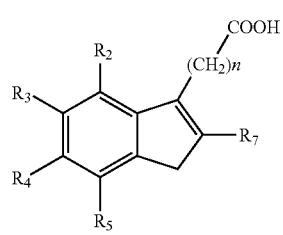

(Ik)

where $R_2$, $R_3$, $R_4$, $R_5$, $R_7$ and n have the meanings described above.

In a different aspect, the invention refers to the procedures for obtaining the indene derivatives of general formula I. Several procedures have been developed for obtaining the indene derivatives of the invention. Each of these procedures will be explained below.

Method A

First of all, a procedure is described for obtaining indene derivatives with general formula (Ia).

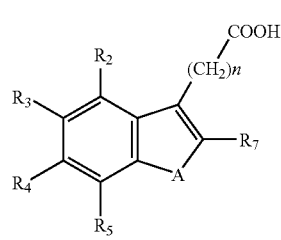

(Ia)

where $R^2$, $R^3$, $R^4$, $R^5$, $R^7$, A and n have the meaning described above, which for the specific case in which n=1 comprises the following steps:

a) bringing together in a suitable reaction media an indanone with general formula II:

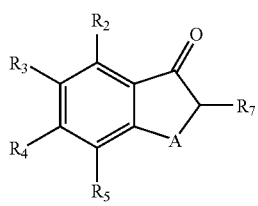

(II)

where $R_2$, $R_3$, $R_4$, $R_5$, $R_7$ and A have the meaning given above, with an alkyl carboxylate to obtain an intermediate alcohol b) Reacting the resulting intermediate alcohol in a solution of an acid, preferably $H_2SO_4$.

In the first stage, very low temperatures approaching −80° C. are used in a reaction media that preferably comprises LHMDS and THF. In addition, it is preferable to carry out this step in an argon atmosphere. In these conditions the indanone of formula II is reacted with an alkyl carboxylate. An intermediate alcohol is obtained from this reaction, which is dried and filtered and then subjected to the second step, which comprises treating the alcohol with an acid, preferably $H_2SO_4$, at a suitable temperature and period of time. The reaction mixture is extracted with an organic acid and after filtering and drying, a precipitate is obtained that can be identified as an acid with general formula (Ia).

Before proceeding with step a) of method A, the indanones of general formula II can be nitrated in positions $R_2$ to $R_5$ as described in D. L. Musso, F. R. Cochran, J. L. Kelley, E. W. McLean, J. L. Selph, G. C. Rigdon, G. F. Orr, R. G. Davis, B. R. Cooper, V. L. Styles, J. B. Thompson, and W. R. Hall, *J. Med. Chem.*, 2003, 46, 399-408.

Method B

This procedure also allows indenylalkylcarboxylic acids to be obtained and comprises three main steps, although the first of these is common to method A. Thus, a procedure is described for obtaining indene derivatives with general formula (Ia):

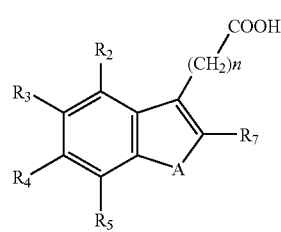

(Ia)

which for the specific case where n=1 comprises the following stages:

a) bringing together in a suitable reaction media an indanone with general formula II:

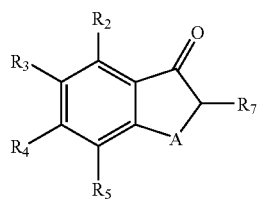

(II)

where $R_2$, $R_3$, $R_4$, $R_5$, $R_7$ and A have the previously mentioned meaning, with an alkyl carboxylate in order to obtain the intermediate alcohol b) adding TFA drop by drop to the resulting intermediate alcohol in a suitable media c) Reacting the resulting mixture with metal sodium dissolved in methanol, bringing the mixture to reflux temperature.

As mentioned before, the step up to the obtaining of the intermediate alcohol is common to method A. The intermediate alcohol obtained is dissolved in a suitable solvent, such as $CH_2Cl_2$, and to this the TFA is added drop by drop at a temperature slightly below 0° C. and preferably while stirring. This mixture is evaporated and re-suspended in a suitable media, such as dry methanol. To this solution a sufficient amount of sodium metal dissolved in the same media in which the previous mixture is re-suspended is added. The resulting mixture is taken to reflux temperature and made to react for a suitable period of time. The product of this reaction mixture is dried and filtered, obtaining a solid that can be identified as an acid with general formula (Ia).

As in method A, the indanones of general formula II can be nitrated in positions $R_2$ to $R_5$ as described in D. L. Musso, F. R. Cochran, J. L. Kelley, E. W. McLean, J. L. Selph, G. C. Rigdon, G. F. Orr, R. G. Davis, B. R. Cooper, V. L. Styles, J. B. Thompson, and W. R. Hall, *J. Med. Chem.*, 2003, 46, 399-408.

On another hand, the compounds of formula (Ia) where n is different from 1 can be prepared via carboxylic acids, according to the methodology described in:

H. Ochiai, T. Nishihara, Y. Tamaru, and Z. Yoshida. Titanium (IV)-Mediated Aldol-Type Condensation of Zinc Esters and Zinc Ketones with Carbonyl Electrophiles. *J. Org. Chem.*, 1988, 53, 1343-1344.

D. A. H. Taylor. 1,2,3,4-Tetrahydro-8-methylfluoren-1-one. *Journal of the Chemical Society, Abstracts*, 1960, 2805-2806.

G. R. Clemo, L. H. Groves, L. Munday, and G. A. Swan. Indene series. I. A synthesis of 1,2,3,8-tetrahydro-1-ketocyclopent[a]indene. *Journal of the Chemical Society, Abstracts*, 1951, 863-867.

M. Finze, S. E. Reybuck, and R. M. Waymouth. Propylene Polymerization with 1,2'-Bridged Bis(indennyl)zirconium Dichlorides. *Macromolecules,* 2003, 36, 9325-9334.

Likewise, the compounds of formula (I) where n is different from 1 may be obtained according to the methodology described in:

R. Perrone, F. Berardi, N. A. Colabufo, V. Tortorella, F. Fiorentini, V. Olgiati, E. Vanotti, and S. Govoni. Mixed 5-HT$_{1A}$/D-2 Activity of a New Model of Arylpiperazines: 1-Aryl-4-[3-(1,2-dihydronaphtalen-4-yl)-n-propyl]piperazines. 1. Synthesis and Structure-Activity Relationships. *J. Med. Chem.,* 1994, 37, 99-104.

K. Fukatsu, O. Uchikawa, M. Kawada, T. Yamano, M. Yamashita, K. Kato, K. Hirai, S. Hinuma, M. Miyamoto, and S. Ohkawa. Synthesis of a Novel Series of Benzocycloalkene Derivatives as Melatonin Receptors Agonists. *J. Med. Chem.,* 2002, 45, 4212-4221.

Method C

In this section a procedure is described for obtaining indene derivatives with general formula (Ib).

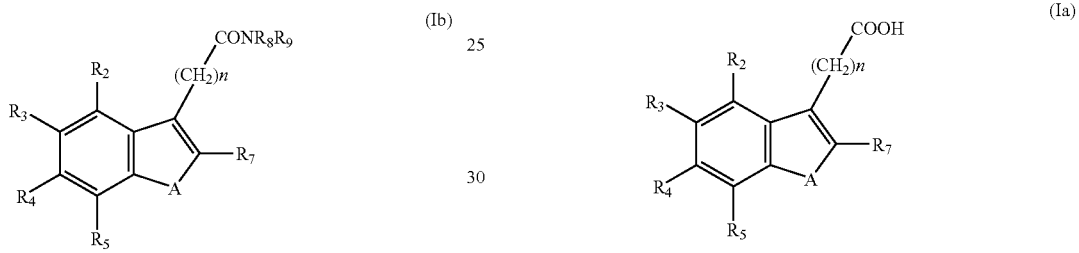

where $R^2$, $R^3$, $R^4$, $R^5$, $R^7$, $R^8$, $R^9$ and A have the previously mentioned meanings and n=0, 1, 2, 3 or 4.

which comprises bringing together in a suitable reaction media an acid with general formula (Ia):

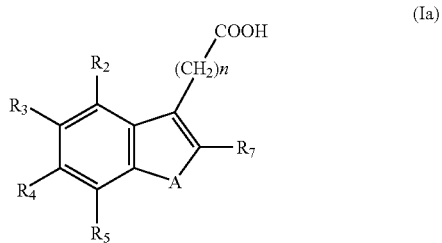

In a sufficient amount of SOCl$_2$ at reflux temperature and adding an amine with the formula NR$^8$R$^9$ to the residue obtained and re-dissolved.

The reaction between the compound with general formula (Ia) and SOCl$_2$ must take place in a suitable media, such as CH$_2$Cl$_2$, and at reflux temperature. The residue obtained after eliminating the excess SOCl$_2$ at reduced pressure is once again dissolved in a suitable media (such as CH$_2$Cl$_2$) and mixed with the amine of general formula NR$^8$R$^9$ at a temperature of about 0° C. The mixture is allowed to react for the required time at room temperature and preferably under stirring.

The product obtained after purification by silica gel column chromatography is characterised as being a compound of general formula (Ib).

Method D

Method D, as method C, provides a procedure for obtaining an indenylamide. Specifically, it is described a procedure for obtaining indene derivatives with general formula (Ib):

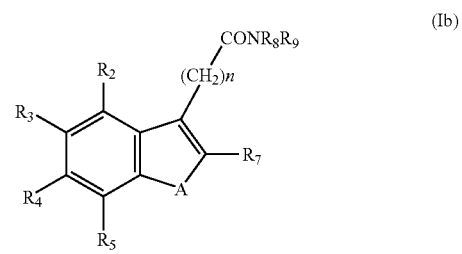

where $R^2$, $R^3$, $R^4$, $R^5$, $R^7$, $R^8$, $R^9$ and A have the previously mentioned meanings and n=0, 1, 2, 3 or 4 which comprises bringing together in a suitable reaction media an acid with general formula (Ia):

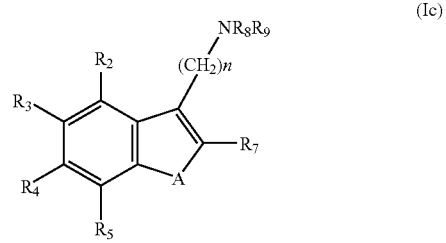

and CDI with stirring and adding an amine with formula NR$^8$R$^9$ to the reaction mixture.

The preferred reaction media for carrying out the reaction between the compound (Ia) and the CDI comprises THF. This reaction, in addition to being favoured by stirring, is also favoured when carried out in an argon atmosphere. On the other hand, the second step in which the amine with the NR$^8$R$^9$ formula is added to the reaction mixture is also preferably carried out with stirring. Both reactions are preferably performed at room temperature for a suitable period of time.

As in the case of method C, after purification by silica gel column chromatography, compounds are obtained that are identified as the compounds of general formula (Ib).

Method E

This section describes a procedure for obtaining an indene derivative with general formula (Ic).

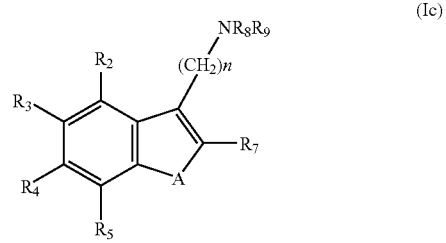

where $R^2$, $R^3$, $R^4$, $R^5$, $R^7$, $R^8$, $R^9$ and A have the previously mentioned meanings and n=0, 1, 2, 3 or 4 which comprises bringing together in a suitable reaction media a compound with general formula (Ib):

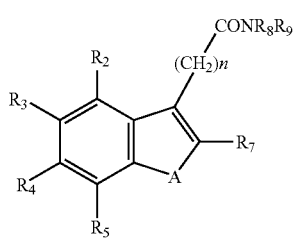
(Ib)

with a solution of AlH$_3$-DMEA.

The reaction is carried out in a reaction media that preferably comprises THF, at temperatures near 0° C. and in an argon atmosphere for a suitable period of time. The residue purified by silica gel column chromatography allows an indenylamine of general formula (Ic) to be identified.

Method F

Method F represents a procedure for preparing an indene derivative of general formula (Id):

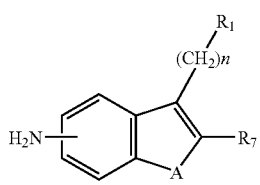
(Id)

where the amine group can be at any position in the benzene ring and the other positions can be substituted as described above for formula I, preferably hydrogen, —OR$_{11}$, —SR$_{11}$, F, Cl, Br, I or a C$_{1-4}$ alkyl radical, and where R$_1$, R$_7$, R$_{11}$, A have the previously mentioned meanings and n=0, 1, 2 3 or 4, which comprises bringing together in a suitable media a compound of general formula (Im):

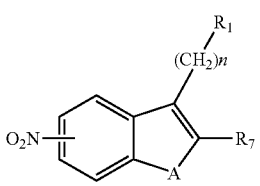
(Im)

where the nitro group can be at any position in the benzene ring and the other positions can be substituted as described above for formula I, preferably hydrogen, —OR$_{11}$, —SR$_{11}$, F, Cl, Br, I or a C$_{1-4}$ alkyl radical, and where R$_1$, R$_7$, R$_{11}$ and A have the meanings given above and n=0, 1, 2, 3 or 4, with a suspension of Zn powder in acetic acid.

The reaction is carried out at room temperature for a suitable period of time, preferably under stirring. Washing with a suitable alkaline aqueous solution confirms that the product obtained is an indenylamine of general formula (Id).

Method G

Method G represents a procedure for preparing an indene derivative of general formula (Ie):

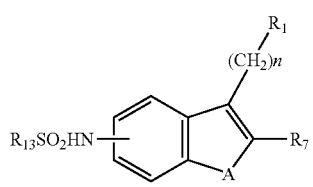
(Ie)

where —NHSO$_2$R$_{13}$ can be at any position in the benzene ring and the other positions can be substituted as described above for formula I, preferably hydrogen, —OR$_{11}$, —SR$_{11}$, F, Cl, Br, I or a C$_{1-4}$ alkyl radical, and where R$_1$, R$_7$, R$_{11}$, R$_{13}$, A have the previously mentioned meanings and n=0, 1, 2 3 or 4, which comprises bringing together in a suitable media a compound of general formula (Id):

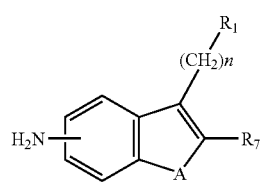
(Id)

where the amine group can be at any position in the benzene ring and the other positions can be substituted as described above for formula I, preferably hydrogen, —OR$_{11}$, —SR$_{11}$, F, Cl, Br, I or a C$_{1-4}$ alkyl radical, and where R$_1$, R$_7$, R$_{11}$, A have the meanings given above and n=0, 1, 2, 3 or 4, with a solution of R$^{13}$SO$_2$Cl at room temperature.

The indenylamine of formula (Id) is made to react dissolved in a suitable media, preferably dry pyridine, with the R$^{13}$SO$_2$Cl also dissolved at room temperature and in an argon atmosphere for a suitable period of time. Purification in silica gel column confirms that the product obtained is a compound of general formula (Ie).

Method H

Method H represents a procedure for preparing an indene derivative of general formula (If):

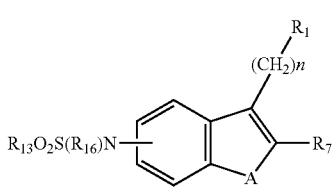
(If)

where —N(R$_{16}$)SO$_2$R$_{13}$ can be at any position in the benzene ring and the other positions can be substituted as described above for formula I, preferably hydrogen, —OR$_{11}$, —SR$_{11}$, F, Cl, Br, I or a C$_{1-4}$ alkyl radical, and where R$_1$, R$_7$, R$_{11}$, R$_{13}$, R$_{16}$, A have the previously mentioned meanings and n=0, 1, 2 3 or 4, which comprises bringing together in a suitable media a compound of general formula (Ie):

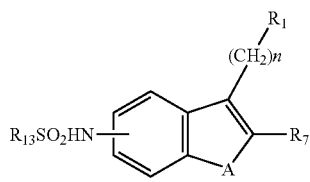

(Ie)

where the amine group can be at any position in the benzene ring and the other positions can be substituted as described above for formula I, preferably hydrogen, —$OR_{11}$, —$SR_{11}$, F, Cl, Br, I or a $C_{1-4}$ alkyl radical, and where $R^1$, $R_7$, $R_{11}$, $R_{13}$, A have the meanings given above and n=0, 1, 2, 3 or 4, with a reaction media comprising $K_2CO_3$ and a suitable alkyl halide at room temperature.

The indenylsulfonamide of formula (Ie) is made to react dissolved in a suitable media, such as acetonitryl, with $K_2CO_3$ and a suitable linear or branched alkyl halide with 1 to 5 carbon atoms also dissolved at room temperature in an argon atmosphere for a suitable period of time. Purification in silica gel column confirms that the product obtained is a compound of general formula (If).

Method I

Method I represents a procedure for preparing an indene derivative of general formula (Ig):

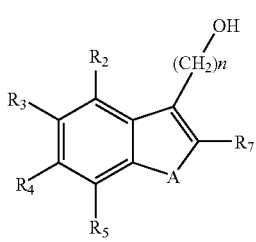

(Ig)

where $R^2$, $R^3$, $R^4$, $R^5$, $R^7$ and A have the previously mentioned meaning and n=1, 2, 3 or 4 that comprises bringing together in a suitable reaction media an indenylic acid of general formula (Ia):

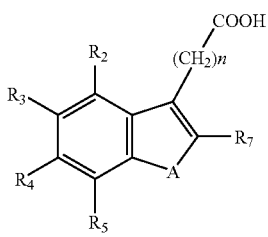

(Ia)

where $R^2$, $R^3$, $R^4$, $R^5$, $R^7$ and A have the meanings given above and n=0, 1, 2, 3 or 4 with a solution of $LiAlH_4$—$AlCl_3$.

The reaction is carried out in a reaction media that preferably comprises THF, at temperatures near 0° C. and in an argon atmosphere for a suitable period of time. The residue purified by silica gel column chromatography allows an alcohol of general formula (Ig) to be identified.

Method J

Method J represents a procedure for preparing an indene derivative of general formula (Ih):

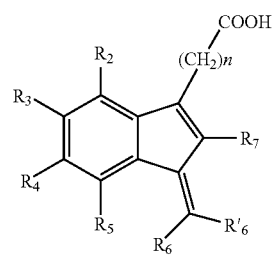

(Ih)

where $R_2$, $R_3$, $R_4$, $R_5$, $R_6$, $R_{6'}$ and $R_7$ have the previously mentioned meanings and n=0, 1, 2, 3 or 4.
which comprises bringing together in a suitable reaction media an indenylic acid with general formula (Ik):

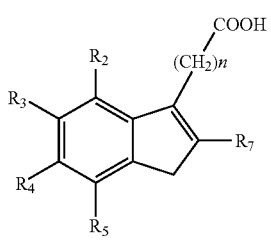

(Ik)

where $R_2$, $R_3$, $R_4$, $R_5$, and $R_7$ have the meanings given above and n=0, 1, 2, 3 or 4, with a reaction media that comprises NaH and a suitable aldehyde at reflux temperature.

The acid with general formula (Ik) is made to react dissolved in a suitable media with NaH and a suitable aldehyde also dissolved at reflux temperature and in an argon atmosphere for a suitable period of time. Acidification and purification in silica gel column of the reaction mixture confirm that the product obtained is an acid of general formula (Ih).

Another essential aspect of the invention are the intermediates for obtaining the compounds of general formula I, general formula (II):

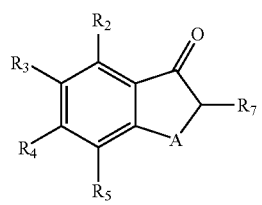

(II)

where $R_2$, $R_3$, $R_4$, $R_5$, $R_7$ and A have the previously mentioned meanings.

The following compounds are specific embodiments of the aforementioned intermediates of formula (II):

[51] 2-Methyl-6-nitroindan-1-one
[52] 2-Methyl-4-nitroindan-1-one
[53] 6-Amino-2-methylindan-1-one
[54] N-(2-Methyl-3-oxoindan-5-yl)naphthalene-2-sulfonamide
[55] 4-Amino-2-methylindan-1-one

[56] N-(2-Methyl-1-oxoindan-4-yl)naphthalene-2-sulfonamide
[57] 6-Nitroindan-1-one
[58] 4-Nitroindan-1-one
[59] 6-Aminoindan-1-one
[60] N-(3-Oxoindan-5-yl)naphthalene-2-sulfonamide
[61] N-(2-Methyl-3-oxoindan-5-yl)-5-chloro-3-methylbenzo[b]thiophene-2-sulfonamide
[62] 2-methyl-3-oxoindan-5-sulfonyl chloride
[63] N-(Naphthalene-1-yl)-2-methyl-3-oxoindano-5-sulfonamide An additional aspect of the invention relates to the therapeutic use of the compounds of general formula I. As mentioned at the beginning, indene derivatives of general formula I have a strong affinity to 5-HT$_6$ receptors and can behave as agonists, antagonists, inverse agonists, partial antagonists or partial agonists thereof. For this reason, they are suitable for the treatment and the prophylaxis of disorders and diseases mediated by 5HT$_6$ receptors. In this sense, indene derivatives of general formula I are particularly useful for disorders or diseases related to food intake, preferably for appetite regulation, maintaining, increasing or reducing body weight, for prophylaxis and/or treatment of obesity, bulimia, anorexia, cachexia or diabetes type II, or for the prophylaxis and/or treatment of irritable bowel syndrome; disorders of the central nervous system; anxiety; panic attacks; depression; bipolar disorders; cognitive disorders; memory disorders; senile dementia; psychosis; schizophrenia; neurodegenerative disorders preferably selected among Alzheimer's disease, Parkinson's disease, Huntington's disease and multiple sclerosis; or hyperactivity disorders, preferably attention deficit/hyperactivity disorder, or for improving cognitive capacity.

Another essential aspect of the invention is a pharmaceutical composition that comprises a compound of general formula I and at least one additive and/or auxiliary material that is pharmaceutically acceptable.

The auxiliary material and/or additive can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

Suitable preparations for oral applications are pills, chewing gums, capsules, granules, drops or syrups.

Suitable preparations for parenteral applications are solutions, suspensions, reconstitutable dry preparations or sprays.

The compounds of the invention as deposits in dissolved form or in patches, optionally with agents that promote skin penetration, are examples of means of percutaneous application.

Skin applications include ointments, gels, creams, lotions, suspensions or emulsions.

The preferred form of rectal application is by means of suppositories.

Optionally, the compositions in accordance with the invention can have a slow release rate in the aforementioned applications, particularly for oral, rectal and percutaneous applications.

The amount of active ingredient that must be administered to the patient depends on the patient's weight, the type of application, the condition and severity of the disease. Normally, in human beings 1 to 500 mg of the active compound are administered daily in one or several doses.

Described below are a number of examples by way of illustration of the invention:

EXAMPLE 1

Synthesis of (2-methyl-6-nitro-3H-inden-1-yl)acetic Acid (Compound 1) Using Method A

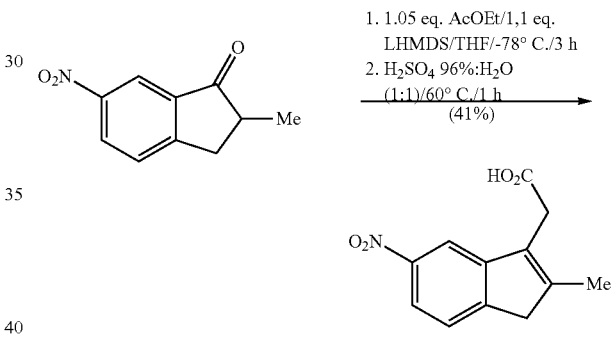

To a sufficient amount of anhydrous THF cooled to −78° C. 1.1-2.1 equivalents of a 1M LHMDS solution in THF were added, in an argon atmosphere. Then 1.05 equivalents of dry AcOEt were added and the resulting mixture was stirred at −78° C. for 30 minutes. Finally, a solution of 1 equivalent of 2-methyl-6-nitroindan-1-one was added in the sufficient amount of anhydrous THF and the resulting mixture was kept at −78° C. for 1-2 hours. The reaction mixture was acidified with HCl 1N, the temperature was allowed to rise gradually until reaching 20° C. and it was extracted with AcOEt. The organic extracts were dried with anhydrous Na$_2$SO$_4$ and filtered, and then evaporated to dryness, giving a residue that was identified by RMN $^1$H as the intermediate alcohol.

The previous alcohol was added to a solution of H$_2$SO$_4$ 50% (1:1), cooled to −5° C., and was heated to 60° C. for 2-5 hours. The progress of the reaction was followed by RMN $^1$H of reaction mixture aliquots. H$_2$O was added to the reaction mixture and it was extracted with AcOEt. The organic extracts, after being dried with anhydrous Na$_2$SO$_4$ and filtered, were evaporated to dryness. The residue obtained was crushed with dry CH$_2$Cl$_2$ and the precipitate obtained was filtered, obtaining a solid that was identified as the indenylacetic acid.

EXAMPLE 2

Synthesis of [2-methyl-6-(naphthalene-2-sulphonylamino)-3H-inden-1-yl]acetic Acid (Compound 2) by Method B

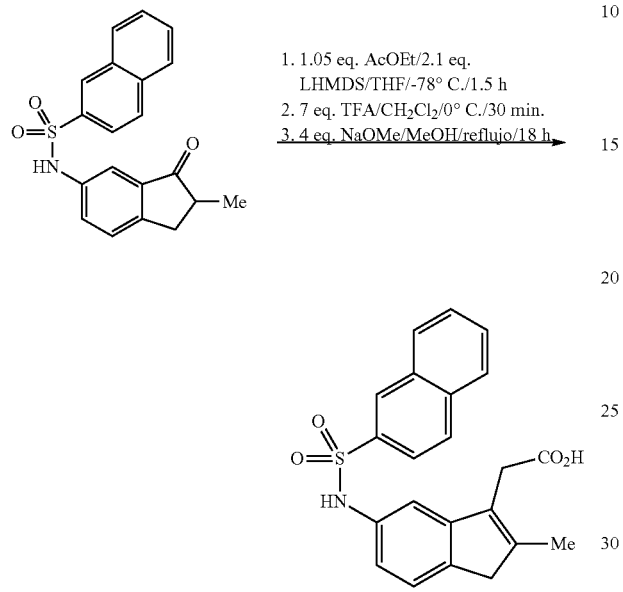

To a sufficient amount of anhydrous THF cooled to −78° C. 1.1-2.1 equivalents of a 1M LHMDS solution in THF were added, in an argon atmosphere. Then 1.05 equivalents of dry AcOEt were added and the resulting mixture was stirred at −78° C. for 30 minutes. Finally, a solution of 1 equivalent of N-(2-methyl-3-oxoindan-5-yl)naphthalene-2-sulfonamide was added in the sufficient amount of anhydrous THF and the resulting mixture was kept at −78° C. for 1-2 hours.

The reaction mixture was acidified with HCl 1N, the temperature was allowed to rise gradually until reaching 20° C. and it was extracted with AcOEt. The organic extracts were dried with anhydrous $Na_2SO_4$ and filtered, and then evaporated to dryness, giving a residue that was identified by RMN $^1$H as the intermediate alcohol.

To a solution of the previous alcohol in dry $CH_2Cl_2$ cooled to −10° C., in an argon atmosphere, 7 equivalents of TFA were added, drop by drop, and it was stirred at the same temperature for 30 minutes. The resulting mixture was evaporated to dryness.

On a sufficient amount of dry methanol, 4 equivalents of sodium metal were added slowly. After all the sodium had dissolved, the solution was transferred to a suspension of the previous residue in dry methanol. The resulting mixture was heated in an argon atmosphere to reflux temperature for 18 hours. The course of the reaction was followed by silica gel thin-layer chromatography (hexane:AcOEt:AcOH 50:45:5).

EtOH was added to the reaction mixture and it was evaporated to dryness. A solution of 5% $Na_2CO_3$ was added to the resulting residue and it was washed with AcOEt. The aqueous solution was acidified with HCl 5N and extracted with AcOEt. The organic extracts, after being dried with anhydrous $Na_2SO_4$ and filtered, were evaporated to dryness obtaining a solid that was identified as [2-methyl-6-(naphthalene-2-sulphonylamino)-3H-inden-1-yl]acetic acid.

EXAMPLE 3

Synthesis of N,N-Dimethyl-2-[2-methyl-6-(naphthalene-2-sulphonylamino)-3H-inden-1-yl]acetamide (Compound 11) by Method C

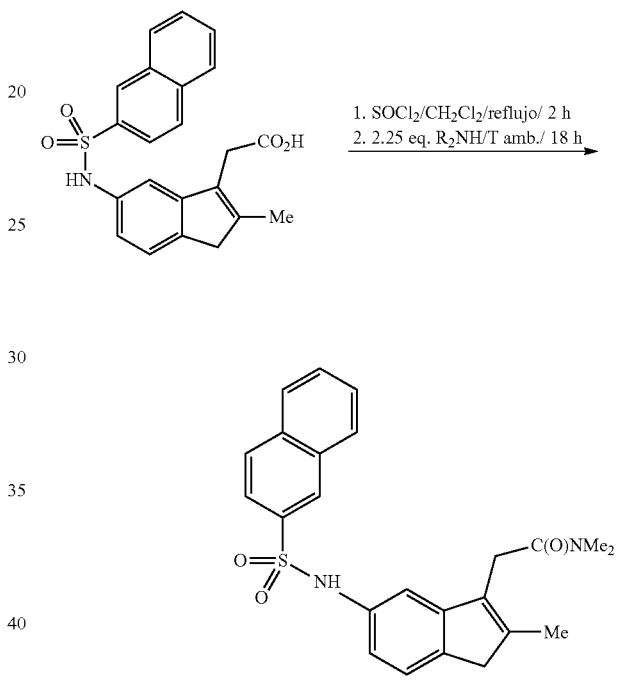

The sufficient amount of $SOCl_2$ was added to a solution of 1 equivalent of the compound obtained in the previous example in dry $CH_2Cl_2$. Then the reaction mixture was heated to reflux temperature for 2 hours. After the reaction mixture had cooled down, the excess $SOCl_2$ was evaporated at reduced pressure.

The residue obtained was dissolved in dry $CH_2Cl_2$, cooled to 0° C., 2.25 equivalents of the amine N,N-dimethylamine were added and it was stirred at room temperature in an argon atmosphere for 18 hours. The course of the reaction was followed by silica gel thin-layer chromatography (AcOEt).

$H_2O$ was added to the reaction mixture; it was acidified with HCl 5N and extracted with AcOEt. The organic extracts, after being dried with anhydrous $Na_2SO_4$ and filtered, were evaporated to dryness. The residue obtained was purified by silica gel column chromatography ($CH_2Cl_2$:MeOH, increasing polarity mixtures), providing a compound identified as N,N-Dimethyl-2-[2-methyl-6-(naphthalene-2-sulphonylamino)-3H-inden-1-yl]acetamide.

EXAMPLE 4

Synthesis of N,N-Dimethyl-2-[2-methyl-6-(naphthalene-2-sulphonylamino)-3H-inden-1-yl]acetamide (Compound 11) by Method D

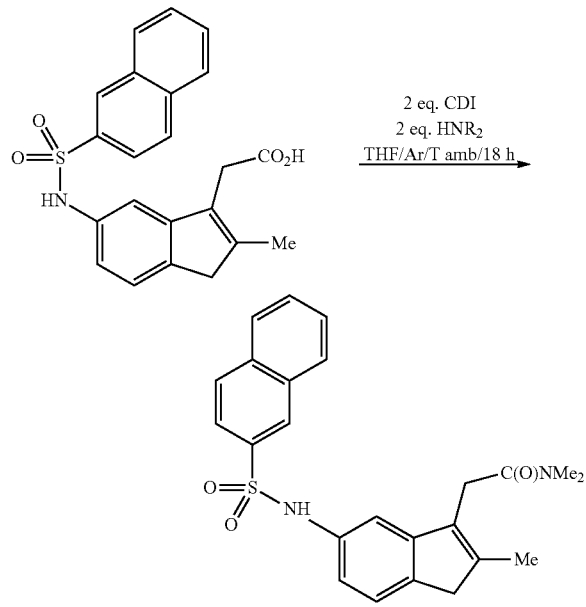

To a solution of 1 equivalent of the compound obtained in example 2 in anhydrous THF, 2 equivalents of CDI were added, in small portions, and it was stirred at room temperature in an argon atmosphere for 2 hours. Subsequently, 2 equivalents of the amine N,N-dimethylamine were added to the reaction mixture and it was kept in stirring at the same temperature for 18 hours. The course of the reaction was followed by silica gel thin-layer chromatography ($CH_2Cl_2$:MeOH 9:1).

The reaction mixture was evaporated to dryness. The residue obtained was dissolved in AcOEt and washed with HCl 1N. The organic extract, after being dried with anhydrous $Na_2SO_4$ and filtered, was evaporated to dryness. The residue obtained was purified by silica gel column chromatography ($CH_2Cl_2$:MeOH, increasing polarity mixtures), providing a compound identified as N,N-Dimethyl-2-[2-methyl-6-(naphthalene-2-sulphonylamino)-3H-inden-1-yl]acetamide.

EXAMPLE 5

Synthesis of N-[3-(2-Dimethylaminoethyl)-2-methyl-1H-inden-5-yl]naphthalene-2-sulfonamide (Compound 34) by Method E

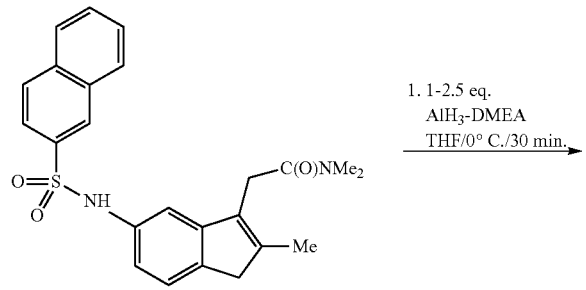

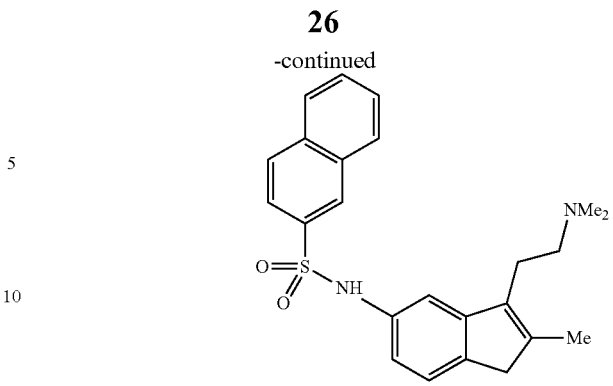

On a sufficient amount of anhydrous THF cooled to 0° C. 1.1-2.5 equivalents of a solution of $AlH_3$-DMEA 0.5M in toluene were added. Then a solution of 1 equivalent was added of the compound obtained in examples 3 or 4 in anhydrous THF cooled to 0° C. At the end of the addition, the mixture was maintained at the same temperature in an argon atmosphere for 30 minutes. The course of the reaction was followed by $SiO_2$ thin-layer chromatography ($CH_2Cl_2$/$NH_3$ gas:MeOH 99:1).

Water and $H_2SO_4$ 10% were added slowly to the reaction mixture and the temperature was allowed to rise slowly to 20° C. It was alkalinised with $NH_3$ 20% and extracted with AcOEt. The organic extracts, after being dried with anhydrous $Na_2SO_4$ and filtered, were evaporated to dryness. The residue obtained was purified by silica gel column chromatography ($CH_2Cl_2$/$NH_3$ gas:MeOH, increasing polarity mixtures), providing a compound identified as N-[3-(2-Dimethylaminoethyl)-2-methyl-1H-inden-5-yl]naphthalene-2-sulfonamide.

EXAMPLE 6

Synthesis of 342-dimethylaminoethyl)-2-methyl-1H-inden-5-ylamine (Compound 18) by Method F

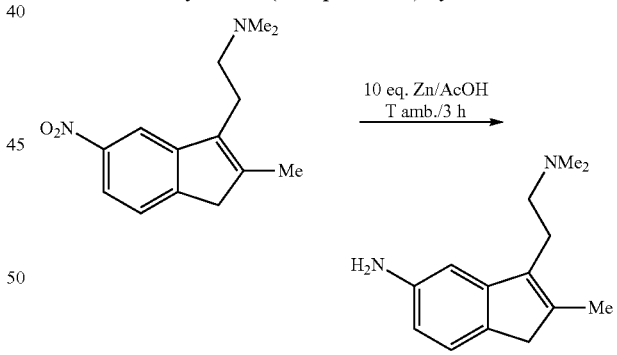

To a solution of 1 equivalent of N,N-dimethyl-[2-(2-methyl-6-nitro-3H-inden-1-yl)ethyl]amine in glacial AcOH 10 equivalents of Zn were added. The resulting suspension was stirred at room temperature for 3 hours. The course of the reaction was followed by silica gel thin-layer chromatography ($CH_2Cl_2$/$NH_3$ gas:MeOH 4:1).

The reaction mixture was filtered through Celite® and the filtered liquids were evaporated to dryness. The residue obtained was dissolved in $CH_2Cl_2$ and washed with $NaHCO_3$ 10%. The organic extract, after being dried with anhydrous $Na_2SO_4$ and filtered, was evaporated to dryness. The residue obtained was purified by silica gel column chromatography ($CH_2Cl_2$/$NH_3$ gas:MeOH, increasing polarity mixtures), obtaining a brown solid identified as 3-(2-dimethylaminoethyl)-2-methyl-1H-inden-5-ylamine.

EXAMPLE 7

Synthesis of Compounds 19, 20, 21 and 22 (Method G)

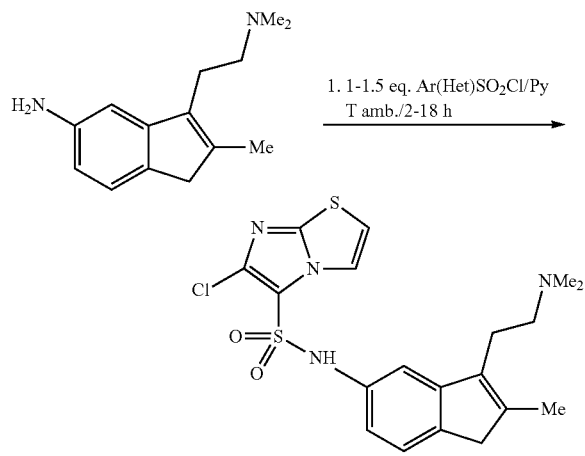

To a solution of 1 equivalent of 3-(2-dimethylaminoethyl)-2-methyl-1H-inden-5-ylamine in dry pyridine a solution of 1.1-1.5 equivalents of 6-chloroimidazo[2,1-b]thiazole-5-sulfonyl chloride in dry pyridine was added. The resulting mixture was stirred at room temperature in an argon atmosphere for 2-18 hours. The course of the reaction was followed by silica gel thin-layer chromatography ($CH_2Cl_2$/$NH_3$ gas: MeOH 4:1).

The reaction mixture was evaporated to dryness. The residue obtained was dissolved in $CH_2Cl_2$ and washed with a saturated solution of $Na_2CO_3$ (3×100 ml). The organic extract, after being dried with anhydrous $Na_2SO_4$ and filtered, was evaporated to dryness. The residue obtained was purified by silica gel column chromatography (($CH_2Cl_2$/$NH_3$ gas: MeOH, increasing polarity mixtures), providing a solid identified as N-[3-(2-Dimethylaminoethyl)-2-methyl-1H-inden-5-yl]-6-chloroimidazo[2,1-b]thiazole-5-sulfonamide.

Compounds 20, 21 and 22 are obtained by the same method from 5-chloro-3-methylbenzo[b]thiophene-2-sulfonyl chloride, 4-acetylaminobenzenosulfonyl chloride and 2,1,3-benzothiadiazole-4-sulfonyl chloride respectively.

EXAMPLE 8

Synthesis of N-ethyl-N-[3-(2-dimethylaminoethyl)-2-methyl-1H-inden-5-yl]-5-chloro-3-methylbenzo[b]thiophene-2-sulfonamide (compound 23) by Method H

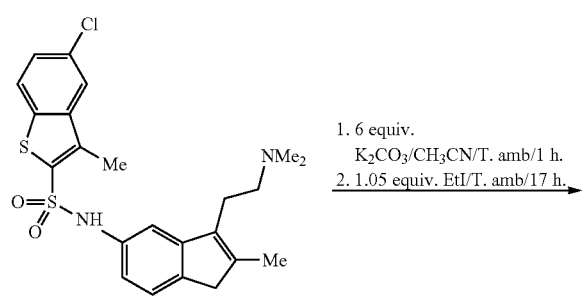

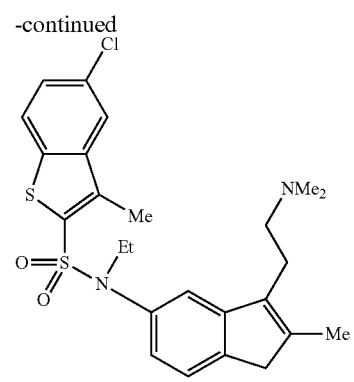

To a solution of 1 equivalent of N-[3-(2-dimethylaminoethyl)-2-methyl-1H-inden-5-yl]-5-chloro-3-methylbenzo[b]thiophene-2-sulfonamide in dry acetonitrile 6 equivalents of potassium carbonate were added. The resulting mixture was stirred at room temperature in an argon atmosphere for 1 hour. Then 1.05 equivalents were added of ethyl iodide and it was kept with stirring at room temperature for 17 hours. The course of the reaction was followed by silica gel thin-layer chromatography ($CH_2Cl_2$/$NH_3$ gas:MeOH 9:1).

The reaction mixture was filtered and the resulting solution was evaporated to dryness, providing a residue that was purified by silica gel chromatography ($CH_2Cl_2$/$NH_3$ gas:MeOH, increasing polarity mixtures), obtaining N-ethyl-N-[3-(2-dimethylaminoethyl)-2-methyl-1H-inden-5-yl]-5-chloro-3-methylbenzo[b]thiophene-2-sulfonamide.

EXAMPLE 9

Synthesis of N-[3-(2-Hydroxyethyl)-2-methyl-1H-inden-5-yl]naphthalene-2-sulfonamide (Compound 40) by Method I

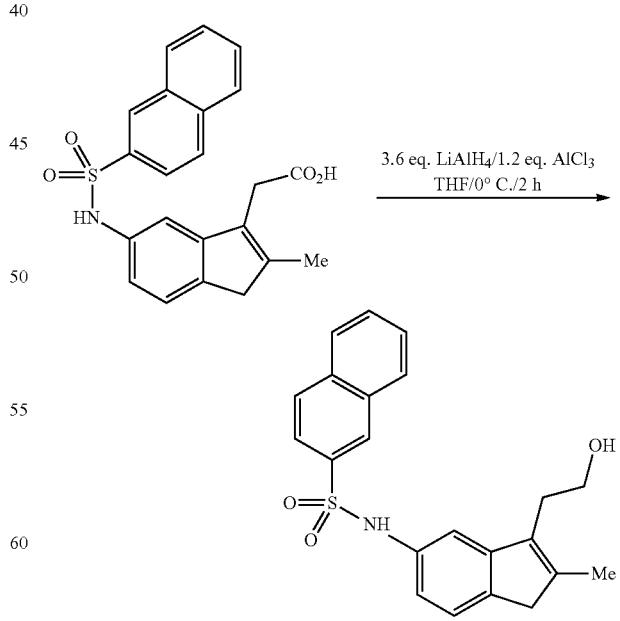

To a suspension of 3.6 equivalents of $LiAlH_4$ in anhydrous THF cooled to 0° C. 1.2 equivalents of $AlCl_3$ were added. The temperature was allowed to rise gradually to 20° C. and stirring in an argon atmosphere was maintained for 1 hour. Then the resulting suspension was cooled to 0° C. and a solution of 1 equivalent of [2-methyl-6-(naphthalene-2-sulphonylamine)-3H-inden-1-yl]acetic acid in anhydrous THF was added, drop by drop. At the end of the addition, stirring was maintained at 0° C. for 2 hours. The course of the reaction was followed by silica gel column chromatography (CH$_2$Cl$_2$: AcOH 95:5).

To the reaction mixture was added HCl 37% and water and extracted with CH$_2$Cl$_2$. Organic extracts were washed with a saturated NaCl solution and, after drying with anhydrous Na$_2$SO$_4$ and filtering, they were evaporated to dryness. A residue was obtained that was purified by silica gel chromatography (CH$_2$Cl$_2$:AcOH 95:5), providing N-[3-(2-hydroxyethyl)-2-methyl-1H-inden-5-yl]naphthalene-2-sulfonamide.

EXAMPLE 10

Synthesis of N-(naphthalene-1-yl)-3-(2-dimethylaminoethyl)-2-methyl-1H-indeno-5-sulfonamide (Compound 39) by Methods B, C and E

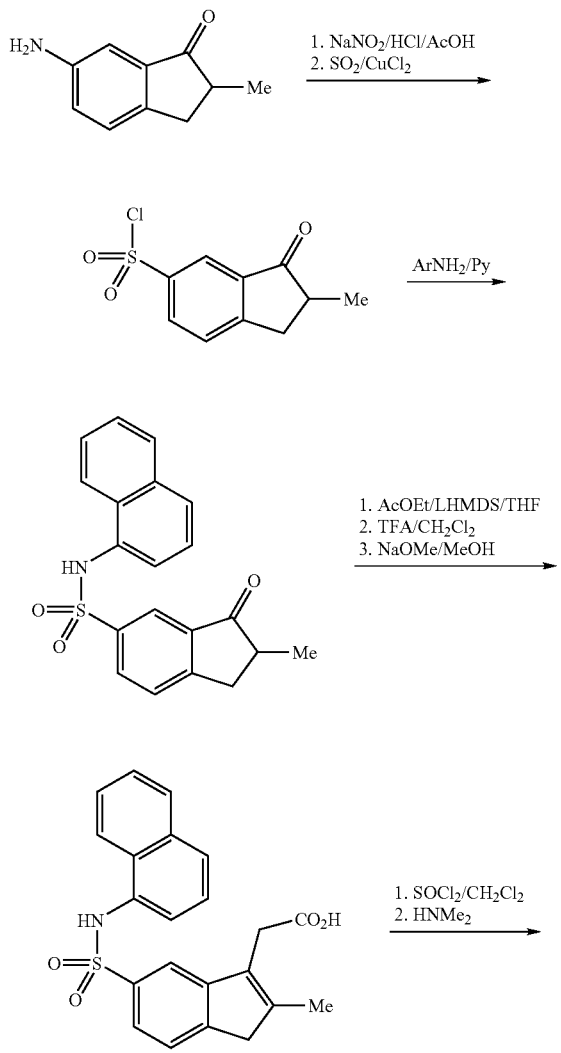

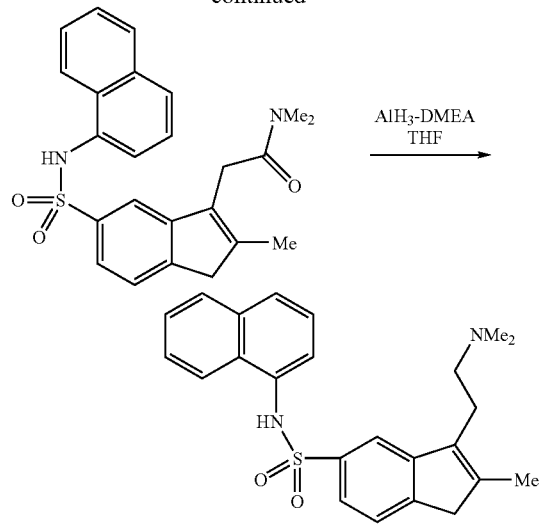

To a solution of 1 equivalent of 6-aminoindan-1-one in CH$_3$CN cooled to −10° C. AcOH glacial, HCl 37% and a solution of 1.2 equivalents of NaNO$_2$ in H$_2$O were added. The resulting mixture was added at the same temperature for 30 minutes. SO$_2$ was bubbled through the reaction mixture for about 20 minutes. Then an H$_2$O solution of 1.25 equivalents of CuCl$_2$.2H$_2$O were added maintaining the temperature at −10° C. The temperature of the reaction mixture was allowed to rise gradually until reaching 20° C. and was stirred for 16 hours. H$_2$O was added to the resulting solution, it was alkalinised with Na$_2$CO$_3$ and extracted with CH$_2$Cl$_2$. The organic extract, after being dried with anhydrous Na$_2$SO$_4$ and filtered, was evaporated to dryness, obtaining an oil that was identified as 2-methyl-3-oxoindane-5-sulfonyl chloride.

To a solution of 1.1 equivalents of 1-naphthylamine in dry CH$_2$Cl$_2$ and dry pyridine a solution of 1 equivalent of the aforementioned sulfonyl chloride in dry CH$_2$Cl$_2$ was added in an argon atmosphere. The reaction mixture was stirred at room temperature for 18 hours. The course of the reaction was followed by silica gel thin-layer chromatography (AcOEt: hexane 1:1). CH$_2$Cl$_2$ was added to the reaction mixture and it was washed with HCl 2.5N. The organic extract, after being dried with anhydrous Na$_2$SO$_4$ and filtered, was evaporated to dryness. The residue obtained was purified by silica gel column chromatography (CH$_2$Cl$_2$:MeOH, increasing polarity mixtures), providing a compound identified by RMN as N-(naphthalene-1-yl)-2-methyl-3-oxoindane-5-sulfonamide.

To a sufficient amount of anhydrous THF cooled to −78° C. 2.1 equivalents of a 1M LHMDS solution in THF were added, in an argon atmosphere. Then 1.05 equivalents of dry AcOEt were added and the resulting mixture was stirred at the same temperature for 30 minutes. Finally, a 1 equivalent solution of the previous indanone in anhydrous THF was added and it was kept stirring for 1 hour at −78° C. The reaction mixture was acidified with HCl 1N, the temperature was allowed to rise gradually until reaching 20° C. and it was extracted with AcOEt. The organic extracts, after being dried with anhydrous Na$_2$SO$_4$ and filtered, were evaporated to dryness. To a solution of the resulting residue in dry CH$_2$Cl$_2$ cooled to −10° C., in an argon atmosphere, 7 equivalents of TFA were added and it was stirred at the same temperature for 30 minutes. The resulting mixture was evaporated to dryness. 4 equivalents of sodium metal were added to a sufficient amount of dry methanol. After all the sodium had dissolved the solution was transferred to a suspension of the previous residue in dry methanol. The resulting mixture was heated in an argon atmosphere to reflux temperature for 18 hours. The course of the reaction was followed by silica gel thin-layer chromatography (hexane:AcOEt:AcOH 50:45:5). EtOH was added to the reaction mixture and it was evaporated to dryness. 5% $Na_2CO_3$ was added to the resulting residue and it was washed with AcOEt. The aqueous solution was acidified with HCl 5N and extracted with AcOEt. The organic extracts, after being dried with anhydrous $Na_2SO_4$ and filtered, were evaporated to dryness obtaining a compound that was identified as [2-methyl-6-(naphthalene-1-ylsulfamoyl)-3H-inden-1-yl]acetic acid.

A sufficient amount of $SOCl_2$ was added to a solution of 1 equivalent of the previous acid in dry $CH_2Cl_2$. Then the reaction mixture was heated to reflux temperature for 2 hours. After the reaction mixture had cooled the excess $SOCl_2$ was evaporated at reduced pressure. To a solution cooled to 0° C. of the residue obtained in dry $CH_2Cl_2$ 2.5 equivalents of $HNMe_2$ were added and it was stirred at room temperature, in an argon atmosphere, for 18 hours. The course of the reaction was followed by silica gel thin-layer chromatography ($CH_2Cl_2$:MeOH 9:1). $H_2O$ was added to the reaction mixture, it was acidified with HCl 5N and extracted with AcOEt. The organic extracts, after being dried with anhydrous $Na_2SO_4$ and filtered, were evaporated to dryness. The residue obtained was purified by silica gel column chromatography ($CH_2Cl_2$:MeOH, increasing polarity mixtures), providing a solid identified as the amide N,N-dimethyl-2-[2-methyl-6-(naphthalene-1-ylsulfamoyl)-3H-inden-1-yl]acetamide.

On a sufficient amount of anhydrous THF cooled to 0° C. 2 equivalents of a solution of $AlH_3$-DMEA 0.5M in toluene were added. Then a solution, previously cooled to 0° C., of 1 equivalent of the previous amide in anhydrous THF was added. It was kept with stirring in an argon atmosphere at 0° C. for 30 minutes. The course of the reaction was followed by silica gel thin-layer chromatography ($CH_2Cl_2/NH_3$ gas: MeOH 95:5). Water and $H_2SO_4$ 10% were added to the reaction mixture and the temperature was allowed to rise slowly to 20° C. It was alkalinised with $NH_3$ 20% and extracted with AcOEt. The organic extracts, after being dried with anhydrous $Na_2SO_4$ and filtered, were evaporated to dryness. The residue obtained was purified by silica gel column chromatography ($CH_2Cl_2/NH_3$ gas:MeOH, increasing polarity mixtures), providing N-(naphthalene-1-yl)-3-(2-dimethylaminoethyl)-2-methyl-1H-indene-5-sulfonamide.

EXAMPLE 11

Synthesis of [3(Z)-benzylidene-2-methyl-6-(naphthalene-2-sulphonylamine)-3H-inden-1-yl]acetic Acid (Compound 3) by Method J

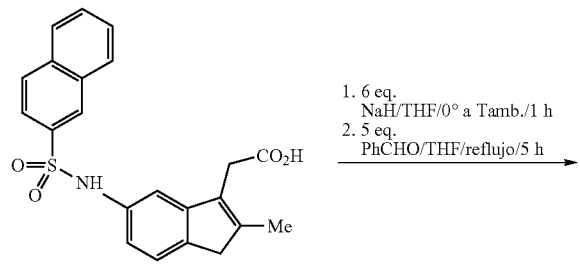

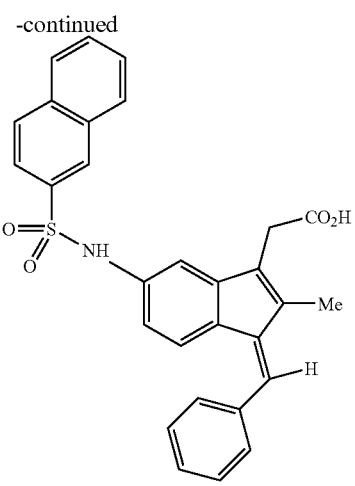

To a suspension of 6 equivalents of NaH in anhydrous THF cooled to 0° C. a solution of 1 equivalent of [2-methyl-6-(naphthalene-2-sulphonylamine)-3H-inden-1-yl]acetic acid in anhydrous THF was added, in an argon atmosphere, and it was stirred at room temperature for 1 hour. Then a solution of 5 equivalents of benzaldehyde in anhydrous THF was added. At the end of the addition the resulting mixture was heated to reflux temperature for 5 hours. The course of the reaction was followed by silica gel thin-layer chromatography (hexane:AcOEt:AcOH 50:45:5).

EtOH was added to the reaction mixture and was evaporated to dryness. A saturated solution of NaCl was added to the resulting residue and was washed with $CH_2Cl_2$. The aqueous solution was acidified with HCl 5N and extracted with $CH_2Cl_2$. After drying with anhydrous $Na_2SO_4$ and filtering, the organic extracts were evaporated to dryness, providing a residue that was purified by silica gel column chromatography (hexane:AcOEt 1:1 and AcOEt). A solid was obtained identified as [3(Z)-benzylidene-2-methyl-6-(naphthalene-2-sulphonylamine)-3H-inden-1-yl]acetic acid.

EXAMPLE 12

Synthesis of 6-chloro-N-[2-methyl-3-(1-methylpyrrolidin-3-yl)-1H-inden-5-yl]imidazo[2,1-b][1,3]thiazole-5-sulfonamide (Compound 45) by Methods E, F and G

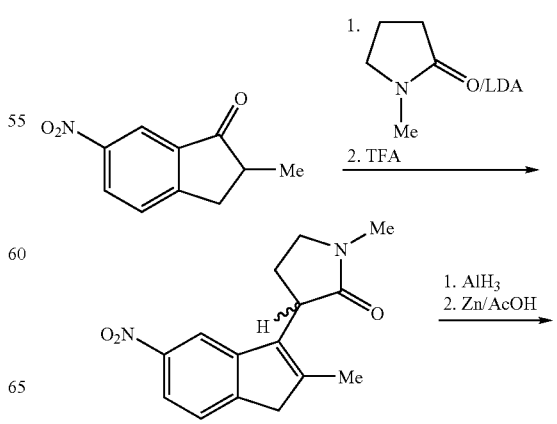

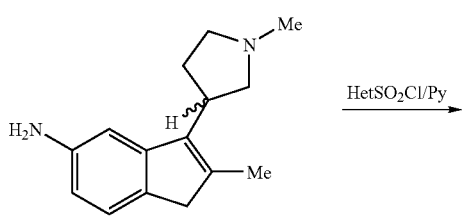

To a stirred solution of LDA (3.84 mL, 5.76 mmol) in THF (20 mL) was added 1-methyl-2-pyrrolidinone (0.53 mL, 5.5 mmol), and the mixture was stirred at dry ice temperature for 1 h. 2-Methyl-6-nitroindan-1-one (1 g, 5.23 mmol) as a solution in 40 mL of THF was then added to the previous mixture. The reaction mixture was stirred for 2 h at dry ice temperature, and transferred to a 1N aqueous HCl solution (50 mL). The aqueous layer was extracted with EtOAc and the extracts were combined and concentrated in vacuum to afford the intermediate alcohol as an oil. To a stirred solution of the previous alcohol in CH$_2$Cl$_2$ (40 mL) was added TFA (3 mL, 40.38 mmol) and the mixture was stirred at ice-water temperature for 30 min. The resulting mixture was evaporated to dryness. The resulting crude was purified by column chromatography on silica gel, using as eluent mixtures of EtOAc/MeOH to afford a lactam as an oil.

To a stirred solution of the previous lactam (322 mg, 1.18 mmol) in 20 mL of THF was added AlH$_3$ (3.8 mL, 1.9 mmol) and the reaction mixture was stirred for 30 min at ice-water temperature. The reaction was quenched by adding a mixture of THF—H2O (1:1, mL) followed by EtOAc (50 mL). The insoluble part was removed by filtration. The combined organic phases were washed with brine and evaporated to afford the intermediate amine as an oil. To a stirred solution of the previous amine in glacial AcOH (5 mL) was added Zn dust (464 mg, 7.1 mmol). After 3 h, the reaction mixture was filtered under vacuum through Celite® and the filtrate was evaporated to dryness to give the corresponding 1H-indenamine as a solid.

To a solution of the previous 1H-indenamine (80 mg, 0.35 mmol) in 3 mL of pyridine, a solution of 6-chloroimidazo[2,1-b][1,3]thiazole-5-sulfonyl chloride in 1 mL of pyridine was added. The reaction mixture was monitored by TLC until completion and then evaporated to dryness. The product was further purified using SiO$_2$ column chromatography with CH$_2$Cl$_2$/MeOH/ammonia yielding 6-chloro-N-[2-methyl-3-(1-methylpyrrolidin-3-yl)-1H-inden-5-yl]imidazo[2,1-b][1,3]thiazole-5-sulfonamide as a solid.

Melting point and the spectroscopic data obtained from some of the compounds of general formula I prepared in accordance with the examples are shown in the following table:

| Ex. | COMPOUND | M.p. °C. | IR cm$^{-1}$ | RMN $^1$H, δ (solvent) |
|---|---|---|---|---|
| 1 | (structure) | 208-10 | 3090, 1703, 1515, 1332 | KBr: 200 MHz (DMSO-d$_6$): 2.09 (s, 3H), 3.52 (s, 2H), 3.57 (s, 2H), 7.60 (d, J = 8.4 Hz, 1H), 7.98-8.02 (m, 2H) |
| 2 | (structure) | 176-8 | 3242, 1705, 1329, 1155 | KBr: 200 MHz (CDCl$_3$): 2.07 (s, 3H), 3.20 (s, 2H), 3.48 (s, 2H), 6.85-6.95 (m, 1H), 7.08-7.18 (m, 2H), 7.40-7.95 (m, 7H), 8.31 (s, 1H) |

-continued

| Ex. | COMPOUND | M.p. °C. | IR cm$^{-1}$ | RMN $^1$H, δ (solvent) |
|---|---|---|---|---|
| 3 | | 110-2 | 3245, 1705, 1330, 1154 | 200 MHz (CDCl$_3$): 2.18 (s, 3H), 3.58 (s, 2H), 7.00 (s, 1H), 7.14-7.17 (m, 2H), 7.33-7.80 (m, 12H), 8.32 (s, 1H) |
| 4 | | 90-2 | 3251, 1703, 1328, 1158 | 200 MHz (CDCl$_3$): 2.04 (s, 3H), 3.15 (s, 2H), 3.45 (s, 2H), 6.82-7.80 (m, 10H), 8.31 (s, 1H) |
| 5 | | 134-6 | 3276, 1702, 1325, 1156 | 200 MHz (CDCl$_3$): 3.15 (s, 2H), 3.49 (s, 2H), 6.37 (s, 1H), 6.90-7.96 (m, 10H), 8.32 (s, 1H) |
| 6 | | 196-8 | 3266, 1710, 1342, 1155 | 200 MHz (CDCl$_3$): 2.10 (s, 3H), 2.32 (s, 3H), 3.28 (s, 2H), 3.48 (s, 2H), 6.86-6.95 (m, 1H), 7.02-7.06 (m, 2H), 7.19-7.33 (m, 2H), 7.58-7.61 (m, 2H) |

| Ex. | COMPOUND | M.p. ° C. | IR cm⁻¹ | RMN ¹H, δ (solvent) |
|---|---|---|---|---|
| 7 | (structure) | 118-20 | KBr: 3251, 1710, 1311, 1151 | 300 MHz (CDCl₃): 2.05 (s, 3H), 3.21 (s, 2H), 3.49 (s, 2H), 7.15-7.32 (m, 4H), 7.38 (dd, J = 1.8, 9.0 Hz, 1H), 7.52-7.57 (m, 2H), 7.64-7.68 (m, 1H), 7.76 (d, J = 1.5 Hz, 1H), 7.85-7.88 (m, 1H) |
| 8 | (structure) | 110-2 | KBr: 1641, 1515, 1342 | 200 MHz (CDCl₃): 2.13 (s, 3H), 2.99 (s, 3H), 3.16 (s, 3H), 3.44 (s, 2H), 3.59 (s, 2H), 7.43 (d, J = 8.8 Hz, 1H), 7.97-8.02 (m, 2H) |
| 9 | (structure) | 128-30 | KBr: 1624, 1513, 1336 | 200 MHz (CDCl₃): 1.86-2.07 (m, 4H), 2.14 (s, 3H), 3.44 (s, 2H), 3.47-3.61 (m, 6H), 7.43 (d, J = 8.0 Hz, 1H), 7.97-8.06 (m, 2H) |
| 10 | (structure) | a | NaCl: 3247, 1606, 1334, 1159 | 200 MHz (CDCl₃): 2.14-2.18 (m, 3H), 2.85-2.98 (m, 6H), 3.49-3.57 (m, 2H), 6.61-6.73 (m, 1H), 7.04-7.83 (m, 14H), 8.32-8.36 (m, 1H) |
| 11 | (structure) | 114-6 | NaCl: 3250, 1610, 1333, 1159 | 200 MHz (CDCl₃): 2.05 (s, 3H), 2.86 (s, 3H), 2.96 (s, 3H), 3.23 (s, 2H), 3.45 (s, 2H), 6.78-7.18 (m, 4H), 7.54-7.94 (m, 5H), 8.38 (s, 1H) |

-continued
| Ex. | COMPOUND | M.p. °C. | IR cm⁻¹ | RMN ¹H, δ (solvent) |
|---|---|---|---|---|
| 12 | 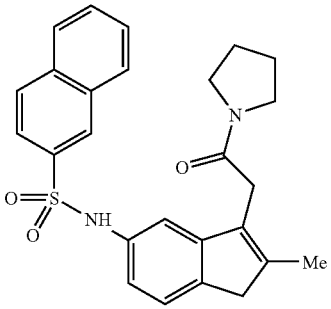 | a | 3063, 1613, 1323, 1156 | KBr: 200 MHz (CDCl₃): 1.65-1.84 (m, 4H), 2.02 (s, 3H), 3.12 (s, 2H), 3.32-3.43 (m, 6H), 6.84-6.89 (m, 1H), 7.01-7.05 (m, 1H), 7.13 (s, 1H), 7.39-7.52 (m, 3H), 7.68-7.79 (m, 4H), 8.33 (s, 1H) |
| 13 | 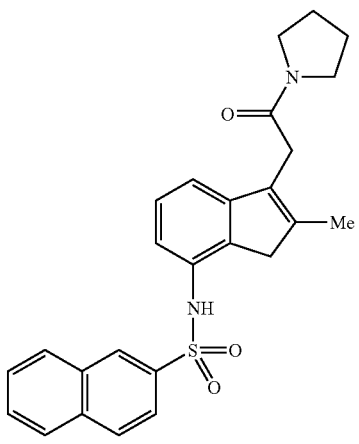 | a | | |
| 14 | 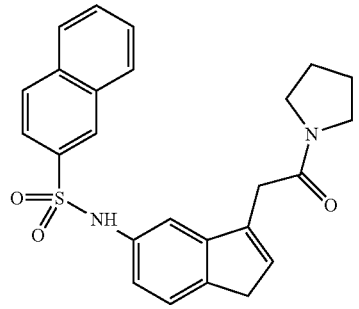 | 125-7 | 3245, 1615, 1326, 1156 | KBr: 200 MHz (CDCl₃): 1.80-2.00 (m, 4H), 3.18 (s, 2H), 3.30-3.50 (m, 4H), 6.30 (s, 1H), 6.95-6.99 (m, 1H), 7.05-7.09 (m, 2H), 7.40-7.58 (m, 2H), 7.64-7.86 (m, 4H), 8.38 (s, 1H) |
| 15 | 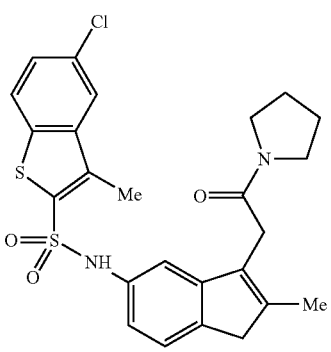 | a | 3079, 1613, 1335, 1157 | KBr: 200 MHz (CDCl₃): 1.78-1.98 (m, 4H), 2.07 (s, 3H), 2.36 (s, 3H), 3.22 (s, 2H), 3.36-3.44 (m, 6H), 6.82-6.88 (m, 1H), 7.08-7.14 (m, 2H), 7.32-7.38 (m, 1H), 7.60-7.64 (m, 2H), 7.82 (s, 1H) |

-continued

| Ex. | COMPOUND | M.p. °C. | IR cm⁻¹ | RMN ¹H, δ (solvent) |
|---|---|---|---|---|
| 16 | (naphthalen-1-ylamino-sulfonyl indene with N,N-dimethylacetamide and 2-Me) | 90-2 | KBr: 3056, 1630, 1314, 1151 | 200 MHz (CDCl₃): 2.02 (s, 3H), 2.91 (s, 3H), 2.99 (s, 3H), 3.20 (s, 2H), 3.45 (s, 2H), 7.17-7.32 (m, 4H), 7.35-7.44 (m, 3H), 7.63-7.67 (m, 1H), 7.74-7.79 (m, 1H), 7.98-8.02 (m, 1H) |
| 17 | (6-nitro-2-methyl-indene with 2-(dimethylamino)ethyl) | a | NaCl: 1520, 1338 | 200 MHz (CDCl₃): 2.13 (s, 3H), 2.35 (s, 6H), 2.42-2.50 (m, 2H), 2.71-2.79 (m, 2H), 7.45 (d, J = 8.0 Hz, 1H), 7.99-8.04 (m, 3H) |
| 18 | (6-amino-2-methyl-indene with 2-(dimethylamino)ethyl) | 68-70 | NaCl: 3343, 3209, 1614, 853, 804 | 200 MHz (CDCl₃): 2.05 (s, 3H), 2.33 (s, 6H), 2.40-2.45 (m, 2H), 2.61-2.69 (m, 2H), 3.18 (s, 2H), 6.46 (dd, J = 2.2, 8.0 Hz, 1H), 6.62 (d, J = 2.2 Hz, 1H), 7.12 (d, J = 8.6 Hz, 1H) |
| 19 | (6-chloroimidazo[2,1-b]thiazole-sulfonamide indene with dimethylaminoethyl and 2-Me) | 200-2 | KBr: 3149, 1343, 1171 | 200 MHz (CDCl₃): 2.03 (s, 3H), 2.26-2.33 (m, 8H), 2.54-2.62 (m, 2H), 3.18 (s, 2H), 6.84 (d, J = 1.8 Hz, 1H), 6.95 (d, J = 4.4 Hz, 1H), 7.04 (dd, J = 1.8, 8.0 Hz, 1H), 7.19 (d, J = 7.8 Hz, 1H), 7.82 (d, J = 4.8 Hz, 1H) |
| 20 | (5-chloro-3-methyl-benzothiophene-2-sulfonamide indene with dimethylaminoethyl and 2-Me) | 158-60 | KBr: 3070, 1337, 1157 | 200 MHz (CDCl₃): 2.01 (s, 3H), 2.31-2.40 (m, 11H), 2.56-2.64 (m, 2H), 3.18 (s, 2H), 6.92-6.99 (m, 2H), 7.18 (d, J = 8.0 Hz, 1H), 7.36 (dd, J = 2.0, 8.0 Hz, 1H), 7.62-7.67 (m, 2H), 8.64 (ba, 1H) |

| Ex. | COMPOUND | M.p. °C. | IR cm⁻¹ | RMN ¹H, δ (solvent) |
|---|---|---|---|---|
| 21 | (structure: 4-acetamidophenyl-SO2-NH-indene with NMe2 and Me) | 116-8 | NaCl: 3263, 1680, 1316, 1157 | 200 MHz (CDCl₃): 2.01 (s, 3H), 2.14 (s, 3H), 2.29-2.40 (m, 8H), 2.54-2.64 (m, 2H), 3.16 (s, 2H), 6.80-6.91 (m, 2H), 7.15 (d, J = 8.0 Hz, 1H), 7.52-7.64 (m, 4H), 8.39 (s, 1H) |
| 22 | (structure: benzothiadiazole-SO2-NH-indene with NMe2 and Me) | 66-8 | NaCl: 2937, 1335, 1158 | 200 MHz (CDCl₃): 1.99 (s, 3H), 2.17-2.24 (m, 2H), 2.28 (s, 6H), 2.48-2.57 (m, 2H), 3,10 (s, 2H), 6.71 (dd, J = 2.0, 7.8 Hz, 1H), 6.85 (d, J = 1.4 Hz, 1H), 7.06 (d, J = 8.0 Hz, 1H), 7.60 (dd, J = 7.0, 8.0 Hz, 1H), 8.15 (dd, J = 1.2, 4.4 Hz, 1H), 8.18-8.20 (m, 1H) |
| 23 | (structure: chlorobenzothiophene-SO2-N(Et)-indene with NMe2 and Me) | a | 1351, 1169 | 200 MHz (CDCl₃): 1.14 (t, J = 6.9 Hz, 3H), 2.07 (s, 3H), 2.00 (s, 3H), 2.14 (s, 6H), 2.17-2.23 (m, 2H), 3.27 (s, 2H), 3.79 (c, J = 6.9 Hz, 2H), 6.89-6.93 (m, 2H), 7.29 (dd, J = 0.9, 9.0 Hz, 1H), 7.42 (dd, J = 1.8, 9.0 Hz, 1H), 7.67 (dd, J = 0.6, 3.0 Hz, 1H), 7.73-7.76 (m, 1H) |
| 24 | (structure: 4-aminophenyl-SO2-NH-indene with NMe2 and Me) | 68-70 | KBr: 3458, 3374, 3236, 1596, 1315, 1149, 829, 676 | 200 MHz (CDCl₃): 2.04 (s, 3H), 2.33-2.40 (m, 8H), 2.57-2.66 (m, 2H), 3.19 (s, 2H), 4.08 (ba, 2H), 6.52-6.59 (m, 2H), 6.81 (dd, J = 2.2, 8.0 Hz, 1H), 6.90 (d, J = 2.0 Hz, 1H), 7.18 (d, J = 8.0 Hz, 1H), 7.49-7.55 (m, 2H) |
| 25 | (structure: 4-OBn-phenylacetamide-indene with pyrrolidine and Me) | a | 3293, 1661 | 200 MHz (CDCl₃): 1.82 (m, 4H), 2.02 (s, 3H), 2.74 (m, 8H), 3.16 (s, 2H), 3.61 (s, 2H), 4.98 (s, 2H), 6.89 (d, J = 8.7 Hz, 2H), 7.19-7.38 (m, 9H), 7.48 (d, J = 1.5 Hz, 1H), 8.44 (s, 1H) |

-continued

| Ex. | COMPOUND | M.p. °C. | IR cm⁻¹ | RMN ¹H, δ (solvent) |
|---|---|---|---|---|
| 26 | (structure: 6-amino-2-methyl-1-[2-(pyrrolidin-1-yl)ethyl]-indene) | 74-76 | KBr: 3440, 3306, 1612, 845, 799 | 200 MHz (CDCl₃): 1.80-1.87 (m, 4H), 2.04 (s, 3H), 2.52-2.78 (m, 8H), 3.17 (s, 2H), 3.68 (ba, 2H), 6.45 (dd, J = 2.2, 8.0 Hz, 1H), 6.64 (d, J = 2.2 Hz, 1H), 7.11 (d, J = 8.0 Hz, 1H) |
| 27 | (structure: chloro-methyl-benzothiophene sulfonamide with ethyl-N,N-dimethyl ammonium iodide indene derivative) | 108-10 | KBr: 1343, 1166 | 200 MHz (CDCl₃): 1.12-1.17 (m, 3H), 1.41 (t, J = 7.2 Hz, 3H), 2.15 (s, 3H), 2.23 (s, 3H), 2.97-3.02 (m, 2H), 3.32 (s, 2H), 3.42 (s, 6H), 3.52-3.58 (m, 2H), 3.76-3.86 (m, 4H), 6.69 (dd, J = 1.6, 6.0 Hz, 1H), 7.1 (dd, J = 1.9, 6.0 Hz, 1H), 7.24 (d, J = 8.0 Hz, 1H), 7.69 (dd, J = 1.8, 6.0 Hz, 1H), 7.73-7.81 (m, 1H) |
| 28 | (structure: 6-nitro-2-methyl-1-[2-(pyrrolidin-1-yl)ethyl]-indene) |  |  | 200 MHz (CDCl₃): 1.81-1.88 (m, 4H), 2.13 (s, 3H), 2.56-2.70 (m, 6H), 2.76-2.84 (m, 2H), 3.37 (s, 2H), 7.44 (dd, J = 0.8, 8.0 Hz, 1H), 7.99-8.08 (m, 2H). |
| 29 | (structure: chloroimidazo[2,1-b]thiazole sulfonamide indene derivative) | 98-100 | KBr: 3112, 1328, 1141 | 200 MHz (CDCl₃): 1.88-1.91 (m, 4H), 2.02 (s, 3H), 2.59-2.72 (m, 8H), 3.18 (s, 2H), 6.84 (d, J = 4.6 Hz, 1H), 6.96 (dd, J = 2.0, 8.0 Hz, 1H), 7.10 (d, J = 1.8 Hz, 1H), 7.17 (d, J = 7.6 Hz, 1H), 7.82 (d, J = 4.4 Hz, 1H) |
| 30 | (structure: 4-acetamidobenzenesulfonamide indene derivative) | 94-6 | KBr: 3256, 1679, 1317, 1155 | 200 MHz (CDCl₃): 1.80-1.81 (m, 4H), 2.04 (s, 3H), 2.17 (s, 3H), 2.45-2.66 (m, 8H), 3.19 (s, 2H), 6.82 (dd, J = 2.1, 8.0 Hz, 1H), 6.91 (d, J = 1.4 Hz, 1H), 7.18 (d, J = 7.6 Hz, 1H), 7.52-7.68 (m, 4H) |

-continued

| Ex. | COMPOUND | M.p. °C. | IR cm⁻¹ | RMN ¹H, δ (solvent) |
|---|---|---|---|---|
| 31 | | 70-2 | KBr: 3257, 1336, 1157 | 200 MHz (CDCl₃): 1.83-1.89 (m, 1H), 1.98 (s, 3H), 2.32-2.41 (m, 2H), 2.56-2.62 (m, 6H), 3.09 (s, 2H), 6.75 (dd, J = 2.0, 8.0 Hz, 1H), 6.86 (d, J = 1.8 Hz, 1H), 7.06 (d, J = 7.6 Hz, 1H), 7.59 (dd, J = 7.0, 8.0 Hz, 1H), 8.12-8.20 (m, 2H) |
| 32 | | 80-2 | KBr: 3452, 3376, 3245, 1596, 1315, 1150, 829, 679 | 200 MHz (CDCl₃): 1.80-1.87 (m, 4H), 2.04 (s, 3H), 2.17-2.71 (m, 8H), 3.19 (s, 2H), 4.07 (s, 2H), 6.52-6.59 (m, 2H), 6.81 (dd, J = 2.2, 8.0 Hz, 1H), 6.92 (d, J = 1.8 Hz, 1H), 7.18 (d, J = 7.6 Hz, 1H), 7.48-7.55 (m, 2H) |
| 33 | | a | | 200 MHz (CDCl₃): 2.10 (s, 3H), 2.28 (s, 6H), 2.28-2.40 (m, 2H), 2.60-2.72 (m, 2H), 6.58-6.64 (m, 1H), 6.88-6.92 (m, 1H), 7.09-7.17 (m, 2H), 7.32-7.86 (m, 13H), 8.38 (s, 1H) |
| 34 | | a | NaCl: 3252, 1329, 1158 | 200 MHz (CDCl₃): 1.99 (s, 3H), 2.23 (s, 6H), 2.23-2.30 (m, 2H), 2.48-2.59 (m, 2H), 3.15 (s, 2H), 6.90-6.93 (m, 2H), 7.14-7.18 (m, 1H), 7.48-7.60 (m, 2H), 7.76-7.86 (m, 4H), 8.35 (s, 1H) |

-continued

| Ex. | COMPOUND | M.p. °C. | IR cm⁻¹ | RMN ¹H, δ (solvent) |
|---|---|---|---|---|
| 35 | (structure) | a | 3250, 1330, 1158 | NaCl: 200 MHz (CDCl₃): 1.70-1.80 (m, 4H), 1.98 (s, 3H), 2.35-2.64 (m, 8H), 3.13 (s, 2H), 6.92-6.97 (m, 2H), 7.13-7.17 (m, 1H), 7.49-7.59 (m, 2H), 7.78-7.85 (m, 4H), 8.36 (s, 1H) |
| 36 | (structure) | a | 3261, 1335, 1160 | NaCl: 400 MHz (CDCl₃): 1.90 (m, 4H), 1.99 (s, 3H), 2.64-2.76 (m, 8H), 3.08 (s, 2H), 6.97-6.99 (m, 1H), 7.05-7.16 (m, 2H), 7.55-7.65 (m, 2H), 7.77-7.80 (m, 1H), 7.85-7.90 (m, 3H), 8.35 (d, J = 1.6 Hz, 1H) |
| 37 | (structure) | | 3056, 1327, 1157 | NaCl: 200 MH, (CDCl₃): 1.70-1.80 (m, 4H), 2.46-2.76 (m, 8H), 3.16 (s, 2H), 6.15 (s, 1H), 7.00-7.06 (m, 2H), 7.20-7.52 (m, 3H), 7.69-7.78 (m, 5H), 8.35 (s, 1H) |
| 38 | (structure) | 186-8 | 1333, 1157 | NaCl: 200 MHz (CDCl₃): 1.80-1.86 (m, 4H), 2.02 (s, 3H), 2.38 (s, 3H), 2.39-2.62 (m, 6H), 3.18 (s, 2H), 6.86 (s, 1H), 7.02-7.10 (m, 1H), 7.15-7.12 (m, 1H), 7.20-7.38 (m, 2H), 7.63-7.67 (m, 1H) |

| Ex. | COMPOUND | M.p. °C. | IR cm⁻¹ | RMN ¹H, δ (solvent) |
|---|---|---|---|---|
| 39 | (naphthalen-1-yl-NH-SO2-indene with NMe2 ethyl and Me) | a | NaCl: 3021, 1316, 1151 | 200 MHz (CDCl₃): 2.05 (s, 3H), 2.33-2.40 (m, 8H), 2.59-2.67 (m, 2H), 3.26 (s, 2H), 7.29-7.46 (m, 5H), 7.55-7.93 (m, 5H) |
| 40 | (naphthalen-2-yl-SO2-NH-indene with hydroxyethyl and Me) | a | | 200 MHz (CDCl₃): 2.01 (s, 3H), 2.62-2.68 (m, 2H), 3.14 (s, 2H), 3.60-3.66 (m, 2H), 6.80-6.88 (m, 1H), 7.05-7.14 (m, 2H), 7.49-7.59 (m, 2H), 7.74-7.80 (m, 4H), 8.36 (s, 1H) |
| 41 | (chloro-imidazothiazole-SO2-NH-indene with NMe2 ethyl and gem-diMe) | Oil | NaCl: 3008, 2935, 1335, 1156 | 200 MHz (CDCl₃): 1.22 (s, 6H), 2.77 s, 6H), 2.80-2.85 (m, 2H), 3.03-3.11 (m, 2H), 6.13 (s, 1H), 6.96 (d, J = 4.4 Hz, 1H), 7.03-7.08 (m, 2H), 7.15-7.19 (m, 1H), 7.77 (d, J = 4.8 Hz, 1H) |
| 42 | (chloro-methyl-benzothiophene-SO2-NH-indene with NMe2 ethyl and gem-diMe) | Oil | NaCl: 3011, 2423, 1332, 1159 | 200 MHz (CDCl₃): 1.23 (s, 6H), 2.37 (s, 3H), 2.71 (s, 6H), 2.74-2.82 (m, 2H), 3.03-3.11 (m, 2H), 6.13 (s, 1H), 6.97 (dd, J = 2.0, 7.8 Hz, 1H), 7.09 (d, J = 1.8 Hz, 1H), 7.15-7.20 (m, 2H), 7.42 (dd, J = 2.0, 8.6 Hz, 1H), 7.68-7.74 (m, 2H) |
| 43 | (naphthalen-1-yl-SO2-NH-indene with NMe2 ethyl and Me) | 200-1 | KBr: 2986, 1320, 1158 | 300 MHz (CDCl₃): 1.98 (s, 3H), 2.18-2.23 (m, 2H), 2.26 (s, 6H), 2.45-2.52 (m, 2H), 3.11 (s, 2H), 6.70 (d, J = 2.9 Hz, 1H), 6.86 (dd, J = 2.0, 9.9 Hz, 1H), 7.09 (d, J = 7.8 Hz, 1H), 7.40-7.46 (m, 1H), 7.53-7.58 (m, 1H), 7.63-7.69 (m, 1H), 7.87-7.90 (m, 1H), 7.98 (d, J = 8.1 Hz, 1H), 8.21 (dd, J = 1.4, 7.2 Hz, 1H), 8.75-8.87 (m, 1H) |

| Ex. | COMPOUND | M.p. °C. | IR cm$^{-1}$ | RMN $^1$H, δ (solvent) |
|---|---|---|---|---|
| 44 | benzothiophene-sulfonamide-indene-NMe$_2$ with Me | 196-7 | KBr: 3117, 1325, 1151 | 400 MHz (CDCl$_3$): 2.00 (s, 3H), 2.20-2.24 (m, 2H), 2.26 (s, 6H), 2.49-2.53 (m, 2H), 3.16 (s, 2H), 6.73 (d, J = 2.0 Hz, 1H), 6.97 (dd, J = 2.0, 7.4 Hz, 1H), 7.16 (d, J = 8.0 Hz, 1H), 7.38-7.47 (m, 2H), 7.81-7.83 (m, 1H), 8.12 (s, 1H); 8.22 (dd, J = 0.8, 7.2 Hz, 1H) |
| 45 | chloro-imidazothiazole-sulfonamide-indene with N-methylpyrrolidinyl and Me | Oil | NaCl: 3118, 3009, 2938, 1334, 1142 | 300 MHz (CDCl$_3$): 2.02-2.04 (s, 5H), 2.53 (s, 3H), 2.63-3.00 (m, 4H), 3.17 (s, 2H), 3.57 (t, J = 8.7 Hz, 1H), 6.85 (d, J = 4.8 Hz, 1H), 7.03 (dd, J = 1.9, 7.5 Hz, 1H), 7.21 (d, J = 7.8 Hz, 1H), 7.41 (d, J = 1.8 Hz, 1H), 7.77 (d, J = 6.0 Hz, 1H) |
| 46 | chloro-imidazothiazole-sulfonamide-indene with N-methylpiperidinyl and Me | Oil | NaCl: 3118, 3009, 2938, 1334, 1142 | 300 MHz (CDCl$_3$): 1.62-1.78 (m, 4H), 1.99-2.05 (m, 5H), 2.36 (s, 3H), 2.74-2.78 (m, 1H), 2.96-3.00 (m, 2H), 3.17 (s, 2H), 6.88 (d, J = 4.2 Hz, 1H), 6.91 (dd, J = 2.1, 7.8 Hz, 1H), 7.18-7.21 (m, 2H), 7.72 (d, J = 4.5 Hz, 1H) |
| 47 | chloro-indene-NMe$_2$ with Me | Oil | NaCl: 2961, 2421, 1467 | 300 MHz (CDCl$_3$): 2.08 (s, 3H), 2.33 (s, 6H), 2.38-2.43 (m, 2H), 2.63-2.68 (m, 2H), 3.24 (s, 2H), 7.06 (dd, J = 1.9, 7.9 Hz, 1H), 7.20 (d, J = 2.1 Hz, 1H), 7.25-7.26 (m, 1H) |
| 48 | chloro-imidazothiazole-sulfonamide-indene-NMe$_2$ | 193-4 | KBr: 3127, 1324, 1118 | 300 MHz (CDCl$_3$): 2.35 (s, 6H), 2.51-2.56 (m, 2H), 2.57-2.67 (m, 2H), 3.24 (s, 2H), 6.24 (s, 1H), 6.98 (d, J = 4.8 Hz, 1H), 7.02 (d, J = 2.1 Hz, 1H), 7.10 (dd, J = 2.1, 8.1 Hz, 1H), 7.30-7.31 (m, 2H), 7.82 (d, J = 4.5 Hz, 1H) |
| 49 | chloro-imidazothiazole-sulfonamide-indene-piperidinyl | 222-3 | KBr: 3124, 1319, 1112 | 300 MHz (CDCl$_3$): 1.50 (m, 2H), 1.65-1.67 (m, 5H), 2.50-2.55 (m, 5H), 2.64 (m, 2H), 3.20-3.23 (m, 2H), 6.23 (s, 1H), 6.95 (d, J = 4.8 Hz, 1H), 7.04 (d, J = 2.1 Hz, 1H), 7.11 (m, 1H), 7.27 (m, 1H), 7.81 (d, J = 4.5 Hz, 1H) |

| Ex. | COMPOUND | M.p. °C. | IR cm⁻¹ | RMN ¹H, δ (solvent) |
|---|---|---|---|---|
| 50 | (chloro-imidazo[2,1-b]thiazole sulfonamide linked to indene with N-methylpyrrolidinyl substituent) | 193-4 | KBr: 3128, 3057, 1319, 1116 | 300 MHz (CDCl₃): 1.81-1.90 (m, 1H), 2.20-2.32 (m, 1H), 2.54 (s, 3H), 2.57-2.74 (m, 2H), 2.92-3.00 (m, 1H), 3.15 (m, 1H), 3.23 (s, 2H), 3.33-3.38 (m, 1H), 5.33 (bs, 1H), 6.23 (s, 1H), 6.86 (d, J = 4.5 Hz, 1H), 7.03-7.09 (m, 2H), 7.25-7.28 (m, 1H), 7.73 (d, J = 4.5 Hz, 1H) |

ᵃOil.

Likewise, the following table shows some of the intermediates of general formula (II) used in accordance with the procedures described herein in order to obtain the compounds of general formula (I), as well as their physicochemical data:

| Ex. | COMPOUND | M.p. °C. | IR cm⁻¹ | RMN ¹H, δ (solvent) |
|---|---|---|---|---|
| 51 | 6-nitro-2-methyl-indan-1-one | 70-2 | NaCl: 1716, 1529, 1348 | 400 MHz (CDCl₃): 1.37 (d, J = 7.2 Hz, 3H); 2.84-2.88 (m, 2H); 3.53 (dd, J = 8.8, 16.0 Hz, 1H); 7.64 (d, J = 8.0 Hz, 1H); 8.45 (dd, J = 2.4, 8.4 Hz, 1H); 8.56 (d, J = 2.0 Hz, 1H) |
| 52 | 4-nitro-2-methyl-indan-1-one | 74-6 | KBr: 1720, 1523, 1353 | 400 MHz (CDCl₃): 1.38 (d, J = 7.2 Hz, 3H); 2.78-2.86 (m, 1H); 3.21 (dd, J = 4.4, 20.0 Hz, 1H); 3.93 (dd, J = 8.0, 16.0 Hz, 1H); 7.62 (dd, J = 7.2, 8.0 Hz, 1H); 8.09 (d, J = 7.2 Hz, 1H); 8.47 (dd, J = 0.8, 8.0 Hz, 1H) |
| 53 | 6-amino-2-methyl-indan-1-one | 144-6 | KBr: 3461, 3358, 1688 | 200 MHz (DMSO-d₆): 1.14 (d, J = 7.4 Hz, 3H), 2.40-2.60 (m, 2H), 3.10-3.25 (m, 1H), 5.28 (ba, 2H), 6.75 (d, J = 1.8 Hz 1H), 6.91 (dd, J = 2.6, 10.0 Hz, 1H), 7.18 (d, J = 8.0 Hz 1H) |
| 54 | N-(2-methyl-1-oxoindan-6-yl)naphthalene-2-sulfonamide | 174-6 | KBr: 3177, 1693, 1341, 1158 | 200 MHz (CDCl₃): 1.24 (d, J = 7.2 Hz, 3H), 2.50-2.80 (m, 2H), 3.20-3.39 (m, 1H), 7.31 (d, J = 10.0 Hz, 1H), 7.43-7.44 (m, 1H), 7.49-7.62 (m, 4H), 7.79-7.90 (m, 4H), 8.39 (s, 1H) |
| 55 | 4-amino-2-methyl-indan-1-one | a | NaCl: 3367, 1694 | 200 MHz (CDCl₃): 1.33 (d, J = 7.4 Hz, 3H), 2.42-2.52 (m, 1H), 2.69-2.75 (m, 1H), 3.11-3.23 (m, 1H), 3.78 (ba, 2H), 6.86-6.90 (m, 1H), 7.21 (d, J = 3.8 Hz, 2H) |

-continued

| Ex. | COMPOUND | M.p. °C. | IR cm$^{-1}$ | RMN $^1$H, δ (solvent) |
|---|---|---|---|---|
| 56 | (structure: N-(2-methyl-1-oxo-2,3-dihydro-1H-inden-4-yl)naphthalene-2-sulfonamide) | 84-6 | KBr: 3241, 1697, 1338, 1159 | 200 MHz, CDCl$_3$-d: 1.06 (d, J = 7.2 Hz, 3H), 2.19-2.29 (m, 1H), 2.42-2.62 (m, 1H), 3.00-3.13 (m, 1H), 6.78 (s, 1H), 7.29 (m, 1H), 7.54-7.95 (m, 8H), 8.33 (d, J = 1.8 Hz, 1H) |
| 57 | (structure: 6-nitro-2,3-dihydro-1H-inden-1-one) | 70-2 b | KBr: 1716, 1541, 1351 | 400 MHz (CDCl$_3$): 2.84 (m, 2H), 3.29 (m, 2H), 7.67 (d, J = 8.4 Hz, 1H), 8.45 (dd, J = 2.0, 8.0 Hz, 1H), 8.57 (d, J = 2.0 Hz, 1H) |
| 58 | (structure: 4-nitro-2,3-dihydro-1H-inden-1-one) | 82-4 b | KBr: 1714, 1520, 1352 | 400 MHz (CDCl$_3$): 2.81 (m, 2H), 3.66 (m, 2H), 7.63 (dd, J = 8.0, 7.6 Hz, 1H), 8.09 (dd, J = 8.0, 0.8 Hz, 1H), 8.48 (dd, J = 1.2, 8.0 Hz, 1H) |
| 59 | (structure: 6-amino-2,3-dihydro-1H-inden-1-one) | 170-2 b | KBr: 3446, 3356, 1677 | 200 MHz (CDCl$_3$): 2.67 (m, 2H), 3.02 (m, 2H), 3.78 (ba, 2H), 7.00 (m, 2H), 7.26 (m, 1H) |
| 60 | (structure: N-(1-oxo-2,3-dihydro-1H-inden-6-yl)naphthalene-2-sulfonamide) | 210-2 | KBr: 3200, 1693, 1334, 1154 | 200 MHz (CDCl$_3$): 2.60-2.67 (m, 2H), 3.01-3.05 (m, 2H), 6.93 (s, 1H), 7.35-7.39 (m, 2H), 7.45-7.78 (m, 4H), 7.82-7.92 (m, 3H), 8.3 (s, 1H) |
| 61 | (structure: 5-chloro-3-methyl-N-(2-methyl-1-oxo-2,3-dihydro-1H-inden-6-yl)benzo[b]thiophene-2-sulfonamide) | 244-6 | KBr: 3120, 1691, 1342, 1158 | 300 MHz (DMSO-d$_6$): 1.28 (d, J = 7.2 Hz, 3H), 2.62-2.90 (m, 2H), 3.36-3.52 (m, 4H), 7.54 (s, 1H), 7.61 (s, 2H), 7.72 (m, 1H), 8.15 (d, J = 2.1 Hz, 1H), 8.21 (d, J = 8.4 Hz, 1H) |

| Ex. | COMPOUND | M.p. °C. | IR cm$^{-1}$ | RMN $^1$H, δ (solvent) |
|---|---|---|---|---|
| 62 | (structure: 6-chlorosulfonyl-2-methyl-indan-1-one) | a | | 200 MHz (CDCl$_3$): 1.37 (d, J = 7.2 Hz, 3H), 2.78-2.98 (m, 2H), 3.46-3.62 (m, 1H), 7.72 (d, J = 8.2 Hz, 1H), 8.23 (dd, J = 1.8, 8.0 Hz, 1H), 8.41 (d, J = 1.4 Hz, 1H) |
| 63 | (structure: naphthalen-1-yl sulfonamide indanone) | 132-4 | KBr: 3274, 1703, 1350, 1159 | 200 MHz (CDCl$_3$): 1.29 (d, J = 7.4 Hz, 3H), 2.66-2.77 (m, 2H), 3.34-3.48 (m, 1H), 6.96 (ba, 1H), 7.37-7.47 (m, 5H), 7.71-7.86 (m, 4H), 8.20 (d, J = 1.0 Hz, 1H) |

Binding Test to 5-HT$_6$ Receptors

Membranes of HEK-293 cells expressing the 5HT$_6$ human recombinant receptor were supplied by Receptor Biology. In these membranes the receptor concentration is 2.18 pmol/mg protein and the protein concentration is 9.17 mg/ml. The experimental protocol follows the method of B. L. Roth et al. [B. L. Roth, S. C. Craigo, M. S. Choudhary, A. Uluer, F. J. Monsma, Y. Shen, H. Y. Meltzer, D. R. Sibley: Binding of Typical and Atypical Antipsychotic Agents to 5-Hydroxytryptamine-6 and Hydroxytriptamine-7 Receptors. *The Journal of Pharmacology and Experimental Therapeutics*, 1994, 268, 1403] with slight modifications. The commercial membrane is diluted (dilution 1:40) with the binding buffer: 50 mM Tris-HCl, 10 mM MgCl$_2$, 0.5 mM EDTA (pH 7.4). The radioligand used is [$^3$H]-LSD at a concentration of 2.7 nM with a final volume of 200 μl. Incubation is initiated by adding 100 μl of the membrane suspension (≈22.9 μg membrane protein), and continues for 60 minutes at a temperature of 37° C. Incubation ends by fast filtration in a Harvester Brandel Cell through glass fibre filters manufactured by Schleicher & Schuell GF 3362 pre-treated with a 0.5% polyethylenimine solution. The filters are washed three times with three milliliters of Tris-HCl 50 mM pH 7.4 buffer. The filters are transferred to vials and to each vial 5 ml of liquid scintillation cocktail Ecoscint H is added. The vials are allowed to reach equilibrium for several hours before being counted in a Wallac Winspectral 1414 scintillation counter. Non-specific binding is determined in the presence of 100 μM serotonin. The tests are performed in triplicate. The inhibition constants ($K_i$, nM) are calculated by non-linear regression analysis using the program EBDA/LIGAND [Munson and Rodbard, *Analytical Biochemistry*, 1980, 107, 220]. The following table shows the binding results for some of the compounds object of the present invention.

| Example | % Inhibition 10$^{-6}$ M | % Inhibition 10$^{-7}$ M | % Inhibition 10$^{-8}$ M | $K_i$ (nM) |
|---|---|---|---|---|
| 19 | 97 | — | — | 4.8 |
| 20 | — | 42 | 13 | — |
| 29 | | 82 | 53 | |
| 32 | | 63 | 26 | |
| 33 | | | | 216.5 |
| 34 | 100 | 71 | 18 | 50.6 |
| 35 | 92 | | | 62.9 |
| 36 | 72 | | | 157.5 |
| 37 | 92 | | | 46.3 |
| 38 | 100 | | | 20.2 |
| 39 | — | 51 | 25 | — |
| 40 | 45 | 16 | 8 | — |
| 41 | | 24.5 | 9.4 | |
| 42 | | 2.3 | −7.5 | |
| 43 | | 78.4 | 32.0 | |
| 44 | | 88.3 | 53.0 | |
| 45 | | 5.4 | 7.4 | |
| 46 | | 85.8 | 77.6 | |
| 47 | | 8.9 | 16.2 | |

Pharmaceutical Formulation

Daily dosage in human medicine lies between 1 mg and 500 mg of product, which can be administered in one or several administrations. The compositions are prepared in forms compatible with the way of administration used, such as pills, tablets, capsules, suppositories, solutions or suspensions. These compositions are prepared by known methods and comprise between 1 to 60% by weight of the active principle (compound of general formula I) and 40 to 99% by weight of a suitable pharmaceutical vehicle compatible with the active principle and the physical form of the composition used. By way of example, the formula is shown for a pill containing a product of the invention.

Example of Formula Per Pill:

| | |
|---|---|
| Example 19 | 5 mg |
| Lactose | 60 mg |
| Crystalline cellulose | 25 mg |
| Povidone K 90 | 5 mg |
| Pregelatinised starch | 3 mg |
| Colloidal silica dioxide | 1 mg |
| Magnesium stereate | 1 mg |
| Total weight per pill | 100 mg |

What is claimed is:

1. An indene derivative of general formula I:

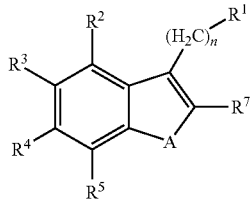

(I)

where n is 0, 1, 2, 3 or 4;

$R^1$ represents a saturated or unsaturated cycloaliphatic radical, optionally at least monosubstituted, optionally at least with one heteroatom selected from N, O and S as a member of the ring that may be condensed with a mono or polycyclic annular system optionally at least monosubstituted; a —$NR^8R^9$ radical; a —$CONR^8R^9$ radical; —COOH; or —OH, where $R^8$ and $R^9$ represent, independently of each other, a hydrogen atom; or a linear or branched, saturated or unsaturated $C_{1-5}$ aliphatic radical that may be substituted by 1, 2, 3 substituents selected independently from F, Cl, Br, —OH, —$NH_2$, —SH, —O—$CH_3$, —O—$C_2H_5$, —$NO_2$, —CN, —NH—$CH_3$ and —S—$CH_3$;

or $R^8$ and $R^9$ together with nitrogen form a saturated, unsaturated or aromatic heterocyclic ring with 3 to 9 members, which may be substituted by 1, 2 or 3 substituents selected independently from $C_{1-5}$-alkyl, —O—$C_{1-5}$-alkyl, —S—$C_{1-5}$-alkyl, oxo (=O), thioxo (=S), —C(=O)—OH, —C(=O)—O—$C_{1-5}$-alkyl, —O—C(=O)—$C_{1-5}$-alkyl, F, Cl, Br, I, —CN, —$CF_3$, —$OCF_3$, —$SCF_3$, —OH, —SH, —$NH_2$, —NH($C_{1-5}$-alkyl), —N($C_{1-5}$-alkyl)$_2$, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl and which may contain 1, 2 or 3 additional heteroatoms independently selected from N, O and S as members of the ring;

$R^2$, $R^3$, $R^4$ and $R^5$ represent, independently of one another, a hydrogen atom; —$NO_2$; —$NH_2$; —SH; —OH; —CN; —C(=O)—H; —C(=O)—$R^{10}$; —$OR^{11}$; —$SR^{12}$; —$SOR^{13}$, —S(=O)$_2$—$R^{13}$, —S(=O)$_2$—N($R^{14}$)$R^{15}$, —N($R^{16}$)—S(=O)$_2$—$R^{17}$; —NH—$R^{18}$; —$NR^{19}R^{20}$; —N($R^{21}$)—CO—$R^{22}$; F; Cl, Br; I; a linear or branched, saturated o unsaturated $C_1$-$C_6$ aliphatic radical, which may be substituted by 1, 2 or 3 substituents independently selected from F, Cl, Br, —OH, —$NH_2$, —SH, —O—$CH_3$, —O—$C_2H_5$, —$NO_2$, —CN, —NH—$CH_3$ and —S—$CH_3$; or an aryl or heteroaryl radical of 5 to 14 members, which may be substituted by 1, 2 or 3 substituents independently selected from —$CF_3$, $C_{1-5}$-alkyl, —O—$C_{1-5}$-alkyl, —S—$C_{1-5}$-alkyl, —C(=O)—OH, —C(=O)—O—$C_{1-5}$-alkyl, —O—C(=O)—$C_{1-5}$-alkyl, F, Cl, Br, I, —CN, —$OCF_3$, —$SCF_3$, —OH, —SH, —$NH_2$, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy, benzyloxy and benzyl and which may be bonded by a linear or branched $C_1$-$C_6$ alkylene group, and where the heteroaryl radical contains 1, 2 or 3 heteroatoms independently selected from N, O and S as members of the ring;

with the condition that at least one of the substituents $R^2$, $R^3$, $R^4$ and $R^5$ represents a —$NO_2$, —$SOR^{13}$, —S(=O)$_2$—$R^{13}$, —S(=O)$_2$—N($R^{14}$)$R^{15}$, —N($R^{16}$)—S(=O)$_2$—$R^{17}$, —N($R^{21}$)—CO—$R^{22}$ radical;

A represents

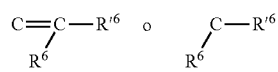

which respectively means (Ix) and (Iy) type compounds

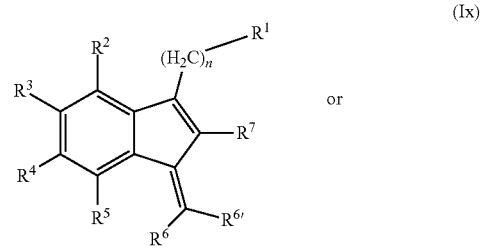

(Ix)

or

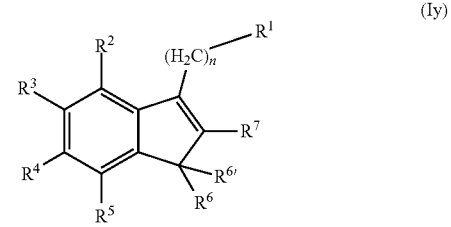

(Iy)

$R^6$ and $R^{'6}$, identical or different, represent a hydrogen atom; $NO_2$; —$NH_2$; —SH; —OH; —CN; —C(=O)—$R^{10}$; —$OR^{11}$; —$SR^{12}$; F; Cl, Br; I; a linear or branched, saturated or unsaturated $C_1$-$C_{10}$ aliphatic radical, which may be substituted with 1, 2 or 3 substituents independently selected among F, Cl, Br, —OH, —SH, —O—$CH_3$, —O—$C_2H_5$, —$NO_2$, —CN and —S—$CH_3$; or an aryl or heteroaryl radical of 5 to 14 members, which may be substituted by 1, 2 or 3 substituents independently selected from —$CF_3$, $C_{1-5}$-alkyl, —O—$C_{1-5}$-alkyl, —S—$C_{1-5}$-alkyl, —C(=O)—OH, —C(=O)—O—$C_{1-5}$-alkyl, —O—C(=O)—$C_{1-5}$-alkyl, F, Cl, Br, I, —CN, —$OCF_3$, —$SCF_3$, —OH, —SH, —$NH_2$, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy, benzyloxy and benzyl and which may be bonded by a linear or branched $C_1$-$C_6$ alkylene, $C_2$-$C_6$ alkenylene or $C_1$-$C_6$ ylidene group, and where the heteroaryl radical contains 1, 2 or 3 heteroatoms independently selected from N, O and S as members of the ring;

63

R⁷ represents a hydrogen atom, a linear or branched $C_1$-$C_6$ aliphatic radical which may be substituted with 1, 2 or 3 substituents independently selected from F, Cl, Br, —OH, —SH, —O—$CH_3$, —O—$C_2H_5$, —$NO_2$, —CN and —S—$CH_3$;

$R^{10}$ to $R^{22}$ represent, independently of each other, a hydrogen atom; a linear or branched, saturated or unsaturated $C_1$-$C_5$ aliphatic radical, which may be substituted by 1, 2 or 3 substituents independently selected from F, Cl, Br, —OH, —$NH_2$, —SH, —O—$CH_3$, —O—$C_2H_5$, —$NO_2$, —CN, —NH—$CH_3$ and —S—$CH_3$; a saturated or unsaturated cycloaliphatic radical with 3 to 8 members, which may be substituted by 1, 2 or 3 substituents independently selected from $C_{1-5}$-alkyl, —O—$C_{1-5}$-alkyl, —S—$C_{1-5}$-alkyl, oxo (=O), thioxo (=S), —C(=O)—OH, —C(=O)—O—$C_{1-5}$-alkyl, —O—C(=O)—$C_{1-5}$-alkyl, F, Cl, Br, I, —CN, —$CF_3$, —$OCF_3$, —$SCF_3$, —OH, —SH, —$NH_2$, —NH($C_{1-5}$-alkyl), —N($C_{1-5}$-alkyl)$_2$, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy benzyloxy and benzyl and which optionally may include 1, 2 or 3 heteroatoms independently selected from N, O and S as members of the ring and which may be bonded through a linear or branched $C_1$-$C_6$ alkylene group; or an aryl or heteroaryl radical with 5 to 14 members that may be substituted by 1, 2 or 3 substituents independently selected from —$CF_3$, $C_{1-5}$-alkyl, —O—$C_{1-5}$-alkyl, —S—$C_{1-5}$-alkyl, —C(=O)—OH, —C(=O)—O—$C_{1-5}$-alkyl, —O—C(=O)—$C_{1-5}$-alkyl, F, Cl, Br, I, —CN, —$OCF_3$, —$SCF_3$, —OH, —SH, —$NH_2$, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy, benzyloxy and benzyl and which may be bonded through a linear or branched $C_1$-$C_6$ alkylene, $C_2$-$C_6$ alkenylene or $C_2$-$C_6$ alkynylene group, and where the heteroaryl radical contains 1, 2 or 3 heteroatoms independently selected from N, O and S as members of the ring;

with the condition that when $R^1$ is —COOH; $R^2$, $R^3$, $R^4$ or $R^5$ are not —$SOR^{13}$, —S(=O)$_2R^{13}$ or —S(=O)$_2$—N($R^{14}$)$R^{15}$ and A does not represent C=C($R^6$)$R'^6$ resulting in the simultaneous situation in which $R^6$ or $R'^6$ are one H and the other a phenyl substituted with —S(=O)$_2$—$C_{1-5}$-alkyl, —$NH_2$, —O—$C_{1-5}$-alkyl, F, Cl, Br, CN, —C(=O)—OH or —C(=O)—O—$C_{1-5}$-alkyl, or the situation in which both $R^6$ and $R'^6$ represent —$OR^{11}$, and with the condition that when $R^1$ is —OH; $R^2$, $R^3$, $R^4$ or $R^5$ are not —S(=O)$_2$—$R^{13}$ or —S(=O)$_2$—N($R^{14}$)$R^{15}$, and with the condition that when $R^1$ is —CONR$^8$R$^9$; $R^2$, $R^3$, $R^4$ or $R^5$ are not —$SOR^{13}$, —S(=O)$_2$—$R^{13}$ or —S(=O)$_2$—N($R^{14}$)$R^{15}$ and A does not represent C=C($R^6$)$R'^6$ resulting in the simultaneous situation in which R6 or $R_6'$ are one H and the other a phenyl substituted with —S(=O)$_2$—$C_{1-5}$-alkyl, —$NH_2$, —O—$C_{1-5}$-alkyl, F, Cl, Br, CN, —C(=O)—OH or —C(=O)—O—$C_{1-5}$-alkyl, an aryl or a heteroaryl, and with the condition that when $R^1$ is —NR$^8$R$^9$; $R^2$, $R^3$, $R^4$ or $R^5$ are not —$SOR^{13}$ or —S(=O)$_2$—$R^{13}$ and A does not represent C=C($R^6$)$R'^6$ resulting in the simultaneous

64 situation in which $R^6$ or $R'^6$ are one H and the other a phenyl substituted with —S(=O)$_2$—$C_{1-5}$-alkyl, —$NH_2$, —O—$C_{1-6}$-alkyl, F, Cl, Br, CN, —C(=O)—OH or —C(=O)—O—$C_{1-5}$-alkyl or a pharmaceutically acceptable salt, isomer or prodrug thereof, optionally in the form of one of their stereoisomers, a racemate or in the form of a mixture of at least two stereoisomers, in any mixing ratio or a physiologically acceptable salt thereof.

2. An indene derivative of general formula I:

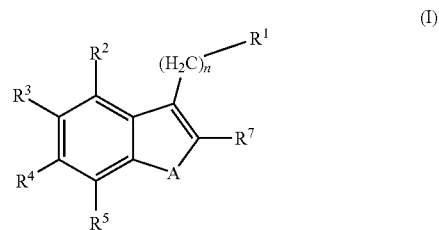

where n is 0, 1, 2, 3 or 4;

$R^1$ represents a saturated or unsaturated cycloaliphatic radical, optionally at least monosubstituted, optionally at least with one heteroatom selected from N, O and S as a member of the ring that may be condensed with a mono or polycyclic annular system optionally at least monosubstituted; a —NR$^8$R$^9$ radical; a —CONR$^8$R$^9$ radical; —COOH; or —OH, where $R^8$ and $R^9$ represent, independently of each other, a hydrogen atom; or a linear or branched, saturated or unsaturated $C_{1-5}$ aliphatic radical that may be substituted by 1, 2, 3 substituents selected independently from F, Cl, Br, —OH, —$NH_2$, —SH, —O—$CH_3$, —O—$C_2H_5$, —$NO_2$, —CN, —NH—$CH_3$ and —S—$CH_3$;

or $R^8$ and $R^9$ together with nitrogen form a saturated, unsaturated or aromatic heterocyclic ring with 3 to 9 members, which may be substituted by 1, 2 or 3 substituents selected independently from $C_{1-5}$-alkyl, —S—$C_{1-5}$-alkyl, oxo (=O), thioxo (=S), —C(=O)—OH, —C(=O)—O—$C_{1-5}$-alkyl, —O—C(=O)—$C_{1-5}$-alkyl, F, Cl, Br, I, —CN, —$CF_3$, —$OCF_3$, —$SCF_3$, —OH, —SH, —$NH_2$, —NH($C_{1-5}$-alkyl), —N($C_{1-5}$-alkyl)$_2$, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, S(=O)$_2$-phenyl and which may contain 1, 2 or 3 additional heteroatoms independently selected from N, O and S as members of the ring;

$R^2$, $R^3$, $R^4$ and $R^5$ represent, independently of one another, a hydrogen atom; —$NO_2$; —$NH_2$; —SH; —OH; —CN; —C(=O)—H; —C(=O)—$R^{10}$; —$OR^{11}$; —$SR^{12}$; —$SOR^{13}$, —S(=O)$_2$—$R^{13}$, —S(=O)$_2$—N($R^{14}$)$R^{15}$, —N($R^{16}$)—S(=O)$_2$—$R^{17}$; —NH—$R^{18}$; —NR$^{19}R^{20}$; —N($R^{21}$)—CO—$R^{22}$; F; Cl, Br; I; a linear or branched, saturated o unsaturated $C_1$-$C_6$ aliphatic radical, which may be substituted by 1, 2 or 3 substituents independently selected from F, Cl, Br, —OH, —$NH_2$, —SH, —O—$CH_3$, —O—$C_2H_5$, —$NO_2$, —CN, —NH—$CH_3$ and —S—$CH_3$; or an aryl or heteroaryl radical of 5 to 14 members, which may be substituted by 1, 2 or 3 substituents independently selected from —CF$_3$, —S—C$_{1-5}$-alkyl, —C(=O)—OH, —C(=O)—O—C$_{1-5}$-alkyl, —O—C(=O)—C$_{1-5}$-alkyl, F, Cl, Br, I, —CN, —OCF$_3$, —SCF$_3$, —OH, —SH, —NH$_2$, —NH(C$_{1-5}$-alkyl), —N(C$_{1-5}$-alkyl)$_2$, —NH—C(=O)—C$_{1-5}$-alkyl, —N(C$_{1-5}$-alkyl)-C(=O)—C$_{1-5}$-alkyl, —NO$_2$, —CHO, —CF$_2$H, —CFH$_2$, —C(=O)—NH$_2$, —C(=O)—NH(C$_{1-5}$-alkyl), —C(=O)—N(C$_{1-5}$-alkyl)$_2$, —S(=O)$_2$-phenyl, cyclopropyl, cyclobutyl, cyclopentyl, cyclohexyl, phenyl, phenoxy, benzyloxy and benzyl and which may be bonded by a linear or branched C$_1$-C$_6$ alkylene group, and where the heteroaryl radical contains 1, 2 or 3 heteroatoms independently selected from N, O and S as members of the ring;

with the condition that at least one of the substituents R$^2$, R$^3$, R$^4$ and R$^5$ represents a —SOR$^{13}$, —S(=O)$_2$—R$^{13}$, —S(=O)$_2$—N(R$^{14}$)R$^{15}$, —N(R$^{16}$)—S(=O)$_2$—R$^{17}$, —N(R$^{21}$)—CO—R$^{22}$ radical;

A represents

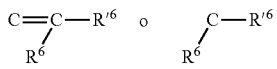

which respectively means (Ix) and (Iy) type compounds

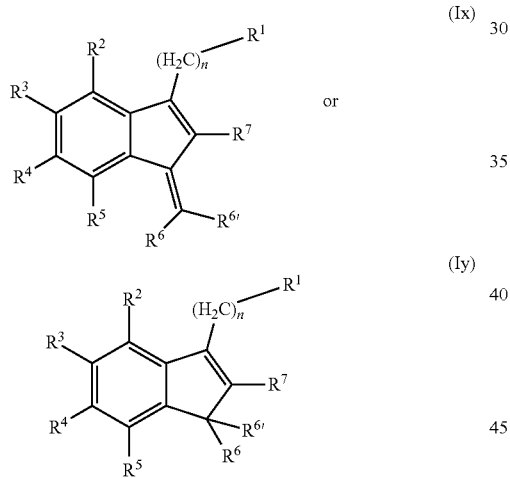

R$^6$ and R$^{'6}$, identical or different, represent a hydrogen atom; NO$_2$; —NH$_2$; —SH; —OH; —CN; —C(=O)—R$^{10}$; —OR$^{11}$; —SR$^{12}$; F; Cl, Br; I; a linear or branched, saturated or unsaturated C$_1$-C$_{10}$ aliphatic radical, which may be substituted by 1, 2 or 3 substituents independently selected from F, Cl, Br, —OH, —SH, —O—CH$_3$, —O—C$_2$H$_5$, —NO$_2$, —CN and —S—CH$_3$; or an aryl or heteroaryl radical of 5 to 14 members, which may be substituted by 1, 2 or 3 substituents independently selected from —CF$_3$, C$_{1-5}$-alkyl, —S—C$_{1-5}$-alkyl, —C(=O)—OH, —C(=O)—O—C$_{1-5}$-alkyl, F, Cl, Br, I, —CN, —OCF$_3$, —SCF$_3$, —OH, —SH, —NH$_2$, —NH(C$_{1-5}$-alkyl), —N(C$_{1-5}$-alkyl)$_2$, —NH—C(=O)—C$_{1-5}$-alkyl, —N(C$_{1-5}$-alkyl)-C(=O)—C$_{1-5}$-alkyl, —NO$_2$, —CHO, —CF$_2$H, —CFH$_2$, —C(=O)—NH$_2$, —C(=O)—NH(C$_{1-5}$-alkyl), —C(=O)—N(C$_{1-5}$-alkyl)$_2$, —S(=O)$_2$-phenyl, cyclopropyl, cyclobutyl, cyclopentyl, cyclohexyl, phenyl, phenoxy, benzyloxy and benzyl and which may be bonded by a linear or branched C$_1$-C$_6$ alkylene, C$_2$-C$_6$ alkenylene or C$_1$-C$_6$ ylidene group, and where the heteroaryl radical contains 1, 2 or 3 heteroatoms independently selected from N, O and S as members of the ring;

R$^7$ represents a hydrogen atom, a linear or branched C$_1$-C$_6$ aliphatic radical which may be substituted by 1, 2 or 3 substituents independently selected from F, Cl, Br, —OH, —SH, —O—CH$_3$, —O—C$_2$H$_5$, —NO$_2$, —CN and —S—CH$_3$;

R$^{10}$ to R$^{22}$ represent, independently of each other, a hydrogen atom; a linear or branched, saturated or unsaturated C$_1$-C$_5$ aliphatic radical, which may be substituted with 1, 2 or 3 substituents independently selected from F, Cl, Br, —OH, —NH$_2$, —SH, —O—CH$_3$, —O—C$_2$H$_5$, —NO$_2$, —CN, —NH—CH$_3$ and —S—CH$_3$; a saturated or unsaturated, cycloaliphatic radical with 3 to 8 members, which may be substituted by 1, 2 or 3 substituents independently selected from C$_{1-5}$-alkyl, —O—C$_{1-6}$-alkyl, —S—C$_{1-5}$-alkyl, oxo (=O), thioxo (=S), —C(=O)—OH, —O—C(=O)—C$_{1-5}$-alkyl, F, Cl, Br, I, —CN, —CF$_3$, —OCF$_3$, —SCF$_3$, —OH, —SH, —NH$_2$, —NH(C$_{1-5}$-alkyl), —N(C$_{1-5}$-alkyl)$_2$, —NO$_2$, —CHO, —CF$_2$H, —CFH$_2$, —C(=O)—NH$_2$, —C(=O)—NH(C$_{1-5}$-alkyl), —C(=O)—N(C$_{1-5}$-alkyl)$_2$, —S(=O)$_2$—C$_{1-5}$-alkyl, —S(=O)$_2$-phenyl, cyclopropyl, cyclobutyl, cyclopentyl, cyclohexyl, phenyl, phenoxy benzyloxy and benzyl and which optionally may include 1, 2 or 3 heteroatoms independently selected from N, O and S as members of the ring and which may be bonded through a linear or branched C$_1$-C$_6$ alkylene group; or an aryl or heteroaryl radical with 5 to 14 members that may be substituted by 1, 2 or 3 substituents independently selected from —CF$_3$, C$_{1-5}$-alkyl, —O—C$_{1-5}$-alkyl, —S—C$_{1-5}$-alkyl, —C(=O)—OH, —C(=O)—O—C$_{1-5}$-alkyl, —O—C(=O)—C$_{1-5}$-alkyl, F, Cl, Br, I, —CN, —OCF$_3$, —SCF$_3$, —OH, —SH, —NH$_2$, —NH(C$_{1-5}$-alkyl), —N(C$_{1-5}$-alkyl)$_2$, —NH—C(=O)—C$_{1-5}$-alkyl, —N(C$_{1-5}$-alkyl)-C(=O)—C$_{1-5}$-alkyl, —NO$_2$, —CHO, —CF$_2$H, —CFH$_2$, —C(=O)—NH$_2$, —C(=O)—NH(C$_{1-5}$-alkyl), —C(=O)—N(C$_{1-5}$-alkyl)$_2$, —S(=O)$_2$—C$_{1-5}$-alkyl, —S(=O)$_2$-phenyl, cyclopropyl, cyclobutyl, cyclopentyl, cyclohexyl, phenyl, phenoxy, benzyloxy and benzyl and which may be bonded through a linear or branched C$_1$-C$_6$ alkylene, C$_2$-C$_6$ alkenylene or C$_2$-C$_6$ alkynylene group, where the heteroaryl radical contains 1, 2 or 3 heteroatoms independently selected from N, O and S as members of the ring;

with the condition that when R$^1$ is —COOH; R$^2$, R$^3$, R$^4$ or R$^5$ are not —SOR$^{13}$, —S(=O)$_2$—R$^{13}$ or —S(=O)$_2$—N(R$^{14}$)R$^{15}$ and A does not represent C=C(R$^6$)R$^{'6}$ resulting in the simultaneous situation in which R$^6$ or R$^{'6}$ are one H and the other a phenyl substituted with —S(=O)$_2$—C$_{1-5}$-alkyl, —NH$_2$, —O—C$_{1-5}$-alkyl, F, Cl, Br, CN, —C(=O)—OH or —C(=O)—O—C$_{1-5}$-alkyl, or the situation in which both R$_6$ and R$_6$' represent —OR$^{11}$, and with the condition that when R$^1$ is —OH; R$^2$, R$^3$, R$^4$ or R$^5$ are not —S(=O)$_2$—R$^{13}$ or —S(=O)$_2$—N(R$^{14}$)R$^{15}$, and with the condition that when R$^1$ is —CONR$^8$R$^9$; R$^2$, R$^3$, R$^4$ o R$^5$ are not —SOR$^{13}$, —S(=O)$_2$—R$^{13}$ or —S(=O)$_2$—N(R$^{14}$)R$^{15}$ and A does not represent C=C(R$^6$)R$^{'6}$ resulting in the simultaneous situation in which R6 or R$_6$' are one H and the other a phenyl substituted by —S (=O)$_2$—C$_{1-5}$-alkyl, —NH$_2$, —O—C$_{1-5}$-alkyl, F, Cl, Br, CN, —C(=O)—OH or —C(=O)—O—C$_{1-5}$-alkyl, an aryl or a heteroaryl, and with the condition that when R$^1$ is —NR$^8$R$^9$; R$^2$, R$^3$, R$^4$ or R$^5$ are not —SOR$^{13}$ or —S(=O)$_2$—R$^{13}$ and A does not represent C=C(R$^6$)R'$^6$ resulting in the simultaneous situation in which R6 or R$_6$' are one H and the other a phenyl substituted by —S(=O)$_2$—C$_{1-5}$-alkyl, —NH$_2$, —O—C$_{1-5}$-alkyl, F, Cl, Br, CN, —C(=O)—OH or —C(=O)—O—C$_{1-5}$-alkyl or a pharmaceutically acceptable salt, isomer or prodrug thereof, optionally in the form of one of their stereoisomers, a racemate or in the form of a mixture of at least two stereoisomers, in any mixing ratio or a physiologically acceptable salt thereof.

3. An indene derivative of general formula (I):

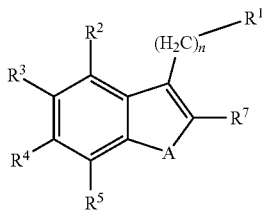

(I)

where n is 0, 1, 2, 3 or 4;

R$^1$ represents a saturated or unsaturated cycloaliphatic radical, optionally at least monosubstituted, optionally at least with one heteroatom selected from N, O and S as a member of the ring that may be condensed with a mono or polycyclic annular system optionally at least monosubstituted; a —NR$^8$R$^9$ radical; a —CONR$^8$R$^9$ radical; —COOH; or —OH, where R$^8$ and R$^9$ represent, independently of each other, a hydrogen atom; or a linear or branched, saturated or unsaturated C$_{1-5}$ aliphatic radical that may be substituted with 1, 2, 3 substituents selected independently from F, Cl, Br, —OH, —NH$_2$, —SH, —O—CH$_3$, —O—C$_2$H$_5$, —NO$_2$, —CN, —NH—CH$_3$ and —S—CH$_3$;

or

R$^8$ and R$^9$ together with nitrogen form a saturated, unsaturated or aromatic heterocyclic ring with 3 to 9 members, which may be substituted by 1, 2 or 3 substituents selected independently from C$_{1-5}$-alkyl, —O—C$_{1-5}$-alkyl, —S—C$_{1-5}$-alkyl, oxo (=O), thioxo (=S), —C(=O)—OH, —C(=O)—O—C$_{1-5}$-alkyl, —O—C(=O)—C$_{1-5}$-alkyl, F, Cl, Br, I, —CN, —CF$_3$, —OCF$_3$, —SCF$_3$, —OH, —SH, —NH$_2$, —NH(C$_{1-5}$-alkyl), —N(C$_{1-5}$-alkyl)$_2$, —NO$_2$, —CHO, —CF$_2$H, —CFH$_2$, —C(=O)—NH$_2$, —C(=O)—NH(C$_{1-5}$-alkyl), —C(=O)—N(C$_{1-5}$-alkyl)$_2$, —S(=O)$_2$—C$_{1-5}$-alkyl, —S(=O)$_2$-phenyl and which may contain 1, 2 or 3 additional heteroatoms independently selected from N, O and S as members of the ring;

R$^2$, R$^3$, R$^4$ and R$^5$ represent, independently of one another, a hydrogen atom; —NO$_2$; —NH$_2$; —SH; —OH; —CN; —C(=O)—H; —C(=O)—R$^{10}$; —OR$^{11}$; —SR$^{12}$; —SOR$^{13}$, —S(=O)$_2$—R$^{13}$, —S(=O)$_2$—N(R$^{14}$)R$^{15}$, —N(R$^{16}$)—S(=O)$_2$—R$^{17}$; —NH—R$^{18}$; —NR$^{19}$R$^{20}$; —N(R$^{21}$)—CO—R$^{22}$; F; Cl; Br; I; a linear or branched, saturated o unsaturated C$_1$-C$_6$ aliphatic radical, which may be substituted by 1, 2 or 3 substituents independently selected from F, Cl, Br, —OH, —NH$_2$, —SH, —O—CH$_3$, —O—C$_2$H$_5$, —NO$_2$, —CN, —NH—CH$_3$ and —S—CH$_3$; or an aryl or heteroaryl radical of 5 to 14 members, which may be substituted by 1, 2 or 3 substituents independently selected from —CF$_3$, C$_{1-5}$-alkyl, —O—C$_{1-5}$-alkyl, —S—C$_{1-5}$-alkyl, —C(=O)—OH, —C(=O)—O—C$_{1-5}$-alkyl, —O—C(=O)—C$_{1-5}$-alkyl, F, Cl, Br, I, —CN, —OCF$_3$, —SCF$_3$, —OH, —SH, —NH$_2$, —NH(C$_{1-5}$-alkyl), —N(C$_{1-5}$-alkyl)$_2$, —NH—C(=O)—C$_{1-5}$-alkyl, —N(C$_{1-5}$-alkyl)-C(=O)—C$_{1-5}$-alkyl, —NO$_2$, —CHO, —CF$_2$H, —CFH$_2$, —C(=O)—NH$_2$, —C(=O)—NH(C$_{1-5}$-alkyl), —C(=O)—N(C$_{1-5}$-alkyl)$_2$, —S(=O)$_2$—C$_{1-5}$-alkyl, —S(=O)$_2$-phenyl, cyclopropyl, cyclobutyl, cyclopentyl, cyclohexyl, phenyl, phenoxy, benzyloxy and benzyl and which may be bonded by a linear or branched C$_1$-C$_6$ alkylene group, and where the heteroaryl radical contains 1, 2 or 3 heteroatoms independently selected from N, O and S as members of the ring;

with the condition that at least one of the substituents R$^2$, R$^3$, R$^4$ and R$^5$ represents a —NO$_2$ radical A represents

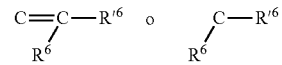

which respectively means (Ix) and (Iy) type compounds

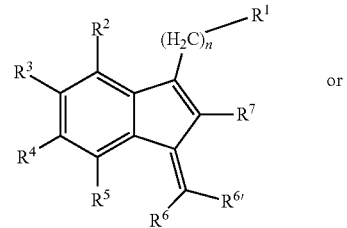

(Ix)

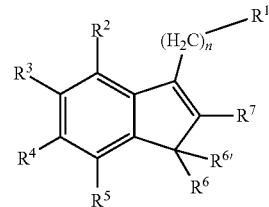

(Iy)

R$^6$ and R'$^6$, identical or different, represent a hydrogen atom; NO$_2$; —NH$_2$; —SH; —OH; —CN; —C(=O)—R$^{10}$; —OR$^{11}$; —SR$^{12}$; F; Cl, Br; I; a linear or branched, saturated or unsaturated C$_1$-C$_{10}$ aliphatic radical, which may be substituted with 1, 2 or 3 substituents independently selected from F, Cl, Br, —OH, —SH, —O—CH$_3$, —O—C$_2$H$_5$, —NO$_2$, —CN and —S—CH$_3$; or an aryl or heteroaryl radical of 5 to 14 members, which may be substituted with 1, 2 or 3 substituents independently selected from —CF$_3$, C$_{1-5}$-alkyl, —O—C$_{1-5}$-alkyl, —S—C$_{1-5}$-alkyl, —C(=O)—OH, —C(=O)—O—C$_{1-5}$-alkyl, —O—C(=O)—C$_{1-5}$-alkyl, F, Cl, Br, I, —CN, —OCF$_3$, —SCF$_3$, —OH, —SH, —NH$_2$, —NH(C$_{1-5}$-alkyl), —N(C$_{1-5}$-alkyl)$_2$, —NH—C(=O)—C$_{1-5}$- alkyl, —N(C alkyl)-C(=O)—$C_{1-5}$-alkyl, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy, benzyloxy and benzyl and which may be bonded by a linear or branched $C_1$-$C_6$ alkylene, $C_2$-$C_6$ alkenylene or $C_1$-$C_6$ ylidene group, and where the heteroaryl radical contains 1, 2 or 3 heteroatoms independently selected from N, O and S as members of the ring;

$R^7$ represents a hydrogen atom, a linear or branched $C_1$-$C_6$ aliphatic radical which may be substituted with 1, 2 or 3 substituents independently selected from F, Cl, Br, —OH, —SH, —O—$CH_3$, —O—$C_2H_5$, —$NO_2$, —CN and —S—$CH_3$;

$R^{10}$ to $R^{22}$ represent, independently of each other, a hydrogen atom; a linear or branched, saturated or unsaturated $C_1$-$C_5$ aliphatic radical, which may be substituted with 1, 2 or 3 substituents independently selected from F, Cl, Br, —OH, —$NH_2$, —SH, —O—$CH_3$, —O—$C_2H_5$, —$NO_2$, —CN, —NH—$CH_3$ and —S—$CH_3$; a saturated or unsaturated cycloaliphatic radical with 3 to 8 members, which may be substituted with 1, 2 or 3 substituents independently selected from $C_{1-5}$-alkyl, —O—$C_{1-5}$-alkyl, —S—$C_{1-5}$-alkyl, oxo (=O), thioxo (=S), —C(=O)—OH, —C(=O)—O—$C_{1-5}$-alkyl, —O—C(=O)—$C_{1-5}$-alkyl, F, Cl, Br, I, —CN, —$CF_3$, —$OCF_3$, —$SCF_3$, —OH, —SH, —$NH_2$, —NH($C_{1-5}$-alkyl), —N($C_{1-5}$-alkyl)$_2$, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy benzyloxy and benzyl and which optionally may include 1, 2 or 3 heteroatoms independently selected from N, O and S as members of the ring and which may be bonded through a linear or branched $C_1$-$C_6$ alkylene group; or an aryl or heteroaryl radical with 5 to 14 members that may be substituted with 1, 2 or 3 substituents independently selected from —$CF_3$, $C_{1-5}$-alkyl, —O—$C_{1-5}$-alkyl, —S—$C_{1-5}$-alkyl, —C(=O)—OH, —C(=O)—O—$C_{1-5}$-alkyl, —O—C(=O)—$C_{1-5}$-alkyl, F, Cl, Br, I, —CN, —$OCF_3$, —$SCF_3$, —OH, —SH, —$NH_2$, —NH($C_{1-5}$-alkyl), —N($C_{1-5}$-alkyl)$_2$, —NH—C(=O)—$C_{1-5}$-alkyl, —N($C_{1-5}$-alkyl)-C(=O)—$C_{1-5}$-alkyl, —$NO_2$, —CHO, —$CF_2H$, —$CFH_2$, —C(=O)—$NH_2$, —C(=O)—NH($C_{1-5}$-alkyl), —C(=O)—N($C_{1-5}$-alkyl)$_2$, —S(=O)$_2$—$C_{1-5}$-alkyl, —S(=O)$_2$-phenyl, cyclopropyl, cyclobutyl, cyclopentyl, cyclohexyl, phenyl, phenoxy, benzyloxy and benzyl and which may be bonded through a linear or branched $C_1$-$C_6$ alkylene, $C_2$-$C_6$ alkenylene or $C_2$-$C_6$ alkynylene group, where the heteroaryl radical contains 1, 2 or 3 heteroatoms independently selected from N, O and S as members of the ring;

with the condition that when $R^1$ is —COOH; $R^2$, $R^3$, $R^4$ or $R^5$ are not —$SOR^{13}$, —S(=O)$_2$—$R^{13}$ or —S(=O)$_2$—N($R^{14}$)$R^{15}$ and A does not represent C=C($R^6$)$R'^6$ resulting in the simultaneous situation in which $R^6$ or $R'^6$ are one H and the other a phenyl substituted with —S(=O)$_2$—$C_{1-5}$-alkyl, —$NH_2$, —O—$C_{1-5}$-alkyl, F, Cl, Br, CN, —C(=O)—OH or —C(=O)—O—$C_{1-5}$-alkyl, or the situation in which both $R_6$ and $R_6'$ represent —$OR^{11}$, and with the condition that when $R^1$ is —OH; $R^2$, $R^3$, $R^4$ or $R^5$ are not —S(=O)$_2$—$R^{13}$ or —S(=O)$_2$—N($R^{14}$)$R^{15}$, and with the condition that when $R^1$ is —CONR$^8$R$^9$; $R^2$, $R^3$, $R^4$ or $R^5$ are not —$SOR^{13}$, —S(=O)$_2$—$R^{13}$ or —S(=O)$_2$—N($R^{14}$)$R^{15}$ and A does not represent C=C($R^6$)$R'^6$ resulting in the simultaneous situation in which R6 or $R_6'$ are one H and the other a phenyl substituted with —S(=O)$_2$—$C_{1-5}$-alkyl, —$NH_2$, —O—$C_{1-5}$-alkyl, F, Cl, Br, CN, —C(=O)—OH or —C(=O)—O—$C_{1-5}$-alkyl, an aryl or a heteroaryl, and with the condition that when $R^1$ is —NR$^8$R$^9$; $R^2$, $R^3$, $R^4$ or $R^5$ are not —$SOR^{13}$ or —S(=O)$_2$—$R^{13}$ and A does not represent C=C($R^6$)$R'^6$ resulting in the simultaneous situation in which $R^6$ or $R'^6$ are one H and the other a phenyl substituted with —S(=O)$_2$—$C_{1-5}$-alkyl, —$NH_2$, —O—$C_{1-5}$-alkyl, F, Cl, Br, CN, —C(=O)—OH or —C(=O)—O—$C_{1-5}$-alkyl or a pharmaceutically acceptable salt, isomer or prodrug thereof, optionally in the form of one of their stereoisomers, a racemate or in the form of a mixture of at least two stereoisomers, in any mixing ratio or a physiologically acceptable salt thereof.

4. An indene derivative of general formula I according to claim 1 where $R^1$ represents a —NR$^8$R$^9$ radical; and $R^8$ and $R^9$ together with nitrogen form a saturated, unsaturated or aromatic heterocyclic ring with 3 to 9 members, which optionally contains 1, 2 or 3 additional heteroatoms independently selected from N, O and S.

5. An indene derivative of general formula I according to claim 1 where $R^1$ represents a —NR$^8$R$^9$ radical; and $R^8$ and $R^9$ represent independently or together a hydrogen atom or a $C_{1-5}$ aliphatic radical.

6. An indene derivative of general formula I according to claim 1, where $R^1$ represents:

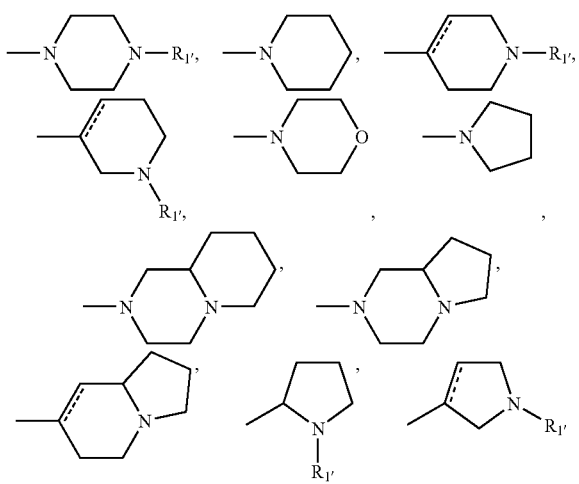

where the dotted line represents an optional chemical bond and $R'_1$ represents a hydrogen atom or a $C_{1-5}$ aliphatic radical.

7. An indene derivative of general formula I according to claim 1 wherein $R^1$ represents a —CONR$^8$R$^9$ radical; and $R^8$ and $R^9$ represent independently or together a hydrogen atom or a $C_{1-5}$ aliphatic radical.

8. An indene derivative of general formula I according to claim 1 where $R^1$ represents a —CONR$^8$R$^9$ radical; and $R^8$ and $R^9$ together with nitrogen form a saturated, unsaturated or aromatic, heterocyclic ring with 3 to 9 members, which optionally contains 1, 2 or 3 additional heteroatoms independently selected from N, O and S.

9. An indene derivative of general formula I according to claim 1 where at least one of $R^2$, $R^3$, $R^4$ and $R^5$ represents a —$SOR^{13}$ radical.

10. An indene derivative of general formula I according to claim 1 where at least one of $R^2$, $R^3$, $R^4$ and $R^5$ represents a —$S(=O)_2$—$R^{13}$ radical.

11. An indene derivative of general formula I according to claim 1 where at least one of $R^2$, $R^3$, $R^4$ and $R^5$ represents a —$S(=O)_2$—$N(R^{14})R^{15}$ radical.

12. An indene derivative of general formula I according to claim 1 where at least one of $R^2$, $R^3$, $R^4$ and $R^5$ represents a —$N(R^{16})$—$S(=O)_2$—$R^{17}$ radical.

13. An indene derivative of general formula I according to claim 1 where at least one of $R^2$, $R^3$, $R^4$ and $R^5$ represents a —$N(R^{21})$—$CO$—$R^{22}$ radical.

14. An indene derivative of general formula I according to claim 1 where $R^6$ or $R'^6$, identical or different, represent a hydrogen atom or an aryl or heteroaryl radical of 5 to 14 members optionally substituted by a phenyl that can be bonded by a $C_1$-$C_6$ alkylene or a $C_1$-$C_6$ ylidene.

15. An indene derivative of general formula I according to claim 1 wherein $R^{10}$ to $R^{22}$ represent an aryl or heteroaryl radical containing 1, 2 or 3 heteroatoms independently selected from N, O and S and which can be substituted by one chlorine atom.

16. An indene derivative of general formula I according to claim 1 where
n=0, 1, 2, 3 or 4; and
$R^1$ represents a —COOH, —OH, —$NR^8R^9$ o —$CONR^8R^9$ radical
where $R^8$ and $R^9$ represent independently or together a hydrogen atom or a $C_{1-5}$ aliphatic radical,
or $R^8$ and $R^9$ together with nitrogen form a saturated, unsaturated or aromatic heterocyclic ring with 3 to 9 members that optionally contains 1, 2 or 3 additional heteroatoms independently selected from N, O and S;
or $R^1$ represents one of the following groups

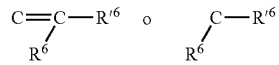

where the dotted line represents an optional chemical bond and $R'_1$ represents a hydrogen atom, a $C_{1-5}$ aliphatic radical; and
where at least one of $R^2$, $R^3$, $R^4$ and $R^5$ represents at least one of a radical $NO_2$; —$NH_2$; —$SOR^{13}$; —$S(=O)_2$—$R^{13}$; —$S(=O)_2$—$N(R^{14})R^{15}$; —$N(R^{16})$—$S(=O)_2$—$R^{17}$; and —$N(R^{21})$—$CO$—$R^{22}$; and any others from $R^2$, $R^3$, $R^4$ and $R^5$ are selected from hydrogen, —$OR_{11}$, —$SR_{11}$, F, Cl, Br, I and a $C_{1-4}$ alkyl radical;
and where A represents

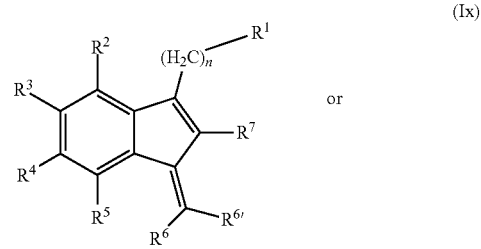

which respectively means (Ix) and (Iy) type compounds

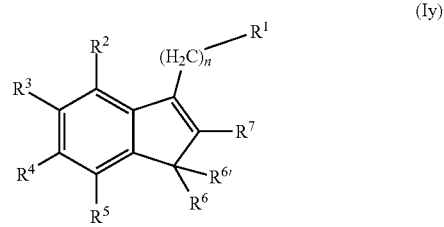

and where $R^6$ and $R'^6$, being identical or different, represent a hydrogen atom or an aryl or heteroaryl radical with 5 to 14 members, optionally substituted by a phenyl that can be bonded through a $C_1$-$C_6$ alkylene or a $C_1$-$C_6$ ylidene; and
where $R^{11}$, $R^{13}$, $R^{14}$, $R^{15}$, $R^{16}$, $R^{17}$, $R^{21}$ and $R^{22}$ represent, independently of one another, a hydrogen atom, a $C_{1-5}$ aliphatic radical, an aryl or heteroaryl radical containing 1, 2 or 3 heteroatoms independently selected among N, O and S and which may be substituted by a chlorine atom.

17. An indene derivative of general formula I according to claim 1, selected from:
[1] (2-methyl-6-nitro-3H-inden-1-yl)acetic acid;
[2] [2-methyl-6-(naphthalene-2-sulphonylamine)-3H-inden-1-yl]acetic acid;
[3] [3(Z)-benzylidene-2-methyl-6-(naphthalene-2-sulphonylamine)-3H-inden-1-yl]acetic acid;
[4] [2-methyl-4-(naphthalene-2-sulphonylamine)-3H-inden-1-yl]acetic acid;
[5] [6-(naphthalene-2-sulphonylamine)-3H-inden-1-yl]acetic acid;
[6] [6-(5-chloro-3-methylbenzo[b]thiophene-2-sulphonylamine)-2-methyl-3H-inden-1-yl]acetic acid;
[7] [2-methyl-6-(naphthalen-1-ylsulfamoyl)-3H-inden-1-yl]acetic acid;
[8] N,N-Dimethyl-2-(2-methyl-6-nitro-3H-inden-1-yl)acetamide;
[9] 2-(2-Methyl-6-nitro-3H-inden-1-yl)-1-pyrrolidin-1-ylethanone;
[10] 2-[3(Z)-Benzylidene-2-methyl-6-(naphthalene-2-sulphonylamine)-3H-inden-1-yl]-N,N-dimethylacetamide;

[11] N,N-Dimethyl-2-[2-methyl-6-(naphthalene-2-sulphonylamine)-3H-inden-1-yl]acetamide;
[12] N-[2-Methyl-3-(2-oxo-2-pyrrolidin-1-ylethyl)-1H-inden-5-yl]naphthalene-2-sulfonamide;
[13] N-[2-Methyl-1-(2-oxo-2-pyrrolidin-1-ylethyl)-3H-inden-4-yl]naphthalene-2-sulfonamide;
[14] N-[3-(2-Oxo-2-pyrrolidin-1-ylethyl)-1H-inden-5-yl]naphthalene-2-sulfonamide;
[15] N-[2-Methyl-3-(2-oxo-2-pyrrolidin-1-ylethyl)-1H-inden-5-yl]-5-chloro-3-methyl benzo[b]thiophene-2-sulfonamide;
[16] N,N-Dimethyl-2-[2-methyl-6-(naphthalen-1-ylsulfamoyl)-3H-inden-1-yl]acetamide;
[17] Dimethyl-[2-(2-methyl-6-nitro-3H-inden-1-yl)ethyl]amine;
[18] 3-(2-Dimethylaminoethyl)-2-methyl-1H-inden-5-ylamine;
[19] N-[3-(2-Dimethylaminoethyl)-2-methyl-1H-inden-5-yl]-6-chloroimidazo[2,1-b]thiazole-5-sulfonamide;
[20] N-[3-(2-Dimethylaminoethyl)-2-methyl-1H-inden-5-yl]-5-chloro-3-methylbenzo [b]thiophene-2-sulfonamide;
[21] N-{4-[3-(2-Dimethylaminoethyl)-2-methyl-1H-inden-5-ylsulfamoyl]phenyl}acetamide;
[22] N-[3-(2-Dimethylaminoethyl)-2-methyl-1H-inden-5-yl]benzo[1,2,5]thiadiazole-4-sulfonamide;
[23] N-Ethyl-N-[3-(2-dimethylaminoethyl)-2-methyl-1H-inden-5-yl]-5-chloro-3-methylbenzo[b]thiophene-2-sulfonamide;
[24] 4-Amino-N-[3-(2-dimethylaminoethyl)-2-methyl-1H-inden-5-yl]benzene sulfonamide;
[25] N-[3-(2-Pyrrolidin-1-ylethyl)-2-methyl-1H-inden-5-yl]-2-(4-benzyloxyphenyl)acetamide;
[26] 2-Methyl-3-(2-pyrrolidin-1-ylethyl)-1H-inden-5-ylamine;
[27] (2-{6-[(5-chloro-3-methylbenzo[b]thiophene-2-sulfonyl)ethylamino]-2-methyl-3H-inden-1-yl}ethyl)ethyldimethylammonium iodide;
[28] 1-[2-(2-Methyl-6-nitro-3H-inden-1-yl)ethyl]pyrrolidine;
[29] N-[3-(2-Pyrrolidin-1-ylethyl)-2-methyl-1H-inden-5-yl]-6-chloroimidazo[2,1-b)]thiazole-5-sulfonamide;
[30] N-{4-[3-(2-Pyrrolidin-1-ylethyl)-2-methyl-1H-inden-5-ylsulfamoyl]phenyl}acetamide;
[31] N-[3-(2-Pyrrolidin-1-ylethyl)-2-methyl-1H-inden-5-yl]-benzo[1,2,5]thiadiazole-4-sulfonamide;
[32] 4-Amino-N-[3-(2-pyrrolidin-1-ylethyl)-2-methyl-1H-inden-5-yl]benzenosulfonamide;
[33] N-[1(Z)-Benzylidene-3-(2-dimethylaminoethyl)-2-methyl-1H-inden-5-yl]naphthalene-2-sulfonamide;
[34] N-[3-(2-Dimethylaminoethyl)-2-methyl-1H-inden-5-yl]naphthalene-2-sulfonamide;
[35] N-[2-Methyl-3-(2-pyrrolidin-1-ylethyl)-1H-inden-5-yl]naphthalene-2-sulfonamide;
[36] N-[2-Methyl-1-(2-pyrrolidin-1-ylethyl)-3H-inden-4-yl]naphthalene-2-sulfonamide;
[37] N-[3-(2-Pyrrolidin-1-ylethyl)-1H-inden-5-yl]naphthalene-2-sulfonamide;
[38] N-[2-Methyl-3-(2-pyrrolidin-1-ylethyl)-1H-inden-5-yl]-5-chloro-3-methylbenzo [b]thiophene-2-sulfonamide;
[39] N-(Naphthalen-1-yl)-3-(2-dimethylaminoethyl)-2-methyl-1H-indeno-5-sulfonamide;
[40] N-[3-(2-Hydroxyethyl)-2-methyl-1H-inden-5-yl]naphthalene-2-sulfonamide;
[41] 6-Chloro-N-{3-[2-(dimethylamino)ethyl]-1,1-dimethyl-1H-inden-5-yl}imidazo[2,1-b][1,3]thiazole-5-sulfonamide;
[42] 5-Chloro-N-{3-[2-(dimethylamino)ethyl]-1,1-dimethyl-1H-inden-5-yl}-3-methylbenzo[b]thiophene-2-sulfonamide;
[43] N-{3-[2-(Dimethylamino)ethyl]-2-methyl-1H-inden-5-yl}naphthalene-1-sulfonamide;
[44] N-{3-[2-(Dimethylamino)ethyl]-2-methyl-1H-inden-5-yl}-1-benzothiophene-3-sulfonamide;
[45] 6-Chloro-N-[2-methyl-3-(1-methylpyrrolidin-3-yl)-1H-inden-5-yl]imidazo[2,1-b][1,3]thiazole-5-sulfonamide;
[46] 6-Chloro-N-[2-methyl-3-(1-methylpiperidin-3-yl)-1H-inden-5-yl]imidazo[2,1-b][1,3]thiazole-5-sulfonamide;
[47] 6-Chloro-N-{3-[2-(dimethylamino)ethyl]-1H-inden-5-yl}imidazo[2,1-b][1,3]thiazole-5-sulfonamide;
[48] 6-Chloro-N-[3-(2-piperidin-1-ylethyl)-1H-inden-5-yl]imidazo[2,1-b][1,3]thiazole-5-sulfonamide; and
[49] 6-Chloro-N-[3-(1-methylpyrrolidin-3-yl)-1H-inden-5-yl]imidazo[2,1-b][1,3]thiazole-5-sulfonamide.

18. An indene derivative according to claim 1 having the general formula (Ia):

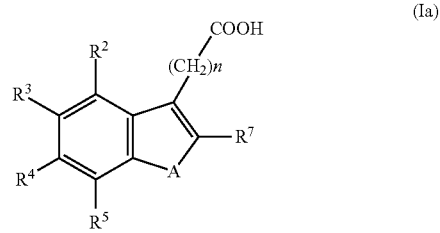

where $R^2$, $R^3$, $R^4$, $R^5$, $R^7$, A are as recited in claim 1, and n=0, 1, 2, 3 or 4.

19. An indene derivative according to claim 1 having the general formula (Ib):

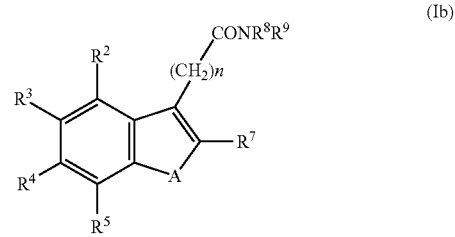

where $R^2$, $R^3$, $R^4$, $R^5$, $R^7$, $R^8$, $R^9$, A are as recited in claim 1 and n=0, 1, 2, 3 or 4.

20. An indene derivative according to claim 1 having the formula (Ic):

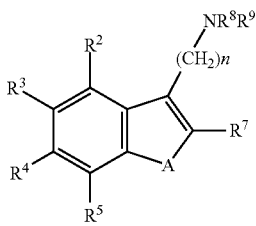

(Ic)

where $R^2$, $R^3$, $R^4$, $R^5$, $R^7$, $R^8$, $R^9$, A are as recited in claim 1 and n=0, 1, 2, 3 or 4.

21. An indene derivative according to claim 1 having the general formula (Id):

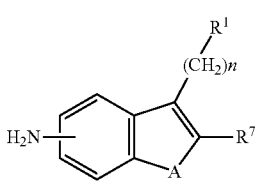

(Id)

where the amine group can be at any position in the benzene ring and in which the other positions can be substituted in accordance with claim 1, and where $R^1$, $R^7$, $R^{11}$ and are as recited in claim 1 and n=0, 1, 2, 3 or 4.

22. An indene derivative according to claim 1 having the general formula (Ie):

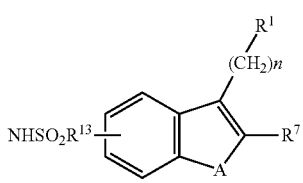

(Ie)

where $NHSO_2R^{13}$ can be at any position in the benzene ring and in which the other positions can be substituted in accordance with claim 1, and where $R^1$, $R^7$, $R^{11}$, $R^{13}$, A are as recited in claim 1 and n=0, 1, 2, 3 or 4.

23. An indene derivative according to claim 1 having the general formula (If):

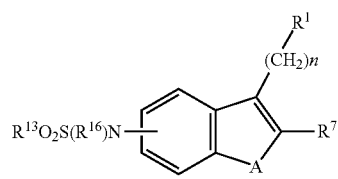

(If)

where $-N(R^{16})SO_2\ R^{13}$ can be at any position in the benzene ring and in which the other positions can be substituted in accordance with claim 1, and where $R^1$, $R^7$, $R^{11}$, $R^{13}$, $R^{16}$, A are as recited in claim 1 and n=0, 1, 2, 3 or 4.

24. An indene derivative according to claim 1 having the general formula (Ig):

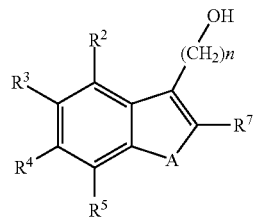

(Ig)

where $R^2$, $R^3$, $R^4$, $R^5$, $R^7$ and A are as recited in claim 1 and n=0, 1, 2, 3 or 4.

25. An indene derivative according to claim 1 having the general formula (Ih):

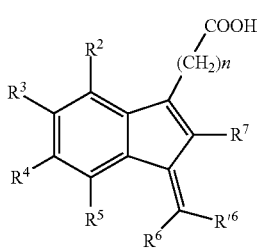

(Ih)

where $R^2$, $R^3$, $R^4$, $R^5$, $R^6$, $R'^6$, $R^7$ are as recited in claim 1 and n=0, 1, 2, 3 or 4.

26. An indene derivative according to claim 1 having the general formula (In):

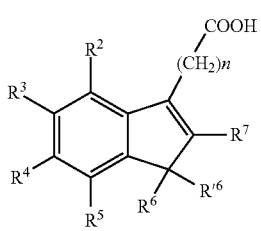

(In)

where $R^2$, $R^3$, $R^4$, $R^5$, $R^6$, $R'^6$, $R^7$ are as recited in claim 1 and n=0, 1, 2, 3 or 4.

27. An indene derivative according to claim 1 having the general formula (Ik):

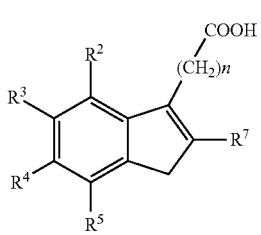

(Ik)

where $R^2$, $R^3$, $R^4$, $R^5$, $R^7$ are as recited in claim 1 and n=0, 1, 2, 3 or 4.

28. A medicament comprising an indene derivative of general formula I according to claim 1.

29. A pharmaceutical composition comprising a compound of general formula I according to claim 1 and at least one pharmaceutically acceptable additive.

* * * * *

UNITED STATES PATENT AND TRADEMARK OFFICE
CERTIFICATE OF CORRECTION

PATENT NO. : 8,217,041 B2
APPLICATION NO. : 12/093100
DATED : July 10, 2012
INVENTOR(S) : Maria de las Ermitas Alcalde-Pais et al.

It is certified that error appears in the above-identified patent and that said Letters Patent is hereby corrected as shown below:

Title Page,

Item (73) Assignee should read:

Laboratorios del Dr. Esteve, S.A. (ES)

Signed and Sealed this
Twenty-fifth Day of September, 2012

David J. Kappos
*Director of the United States Patent and Trademark Office*